(12) United States Patent
Kajita et al.

(10) Patent No.: US 12,114,961 B2
(45) Date of Patent: Oct. 15, 2024

(54) IMAGE PROCESSING APPARATUS AND IMAGE PROCESSING METHOD AND NON-TRANSITORY COMPUTER-READABLE MEDIUM

(71) Applicants: CANON KABUSHIKI KAISHA, Tokyo (JP); KEIO UNIVERSITY, Tokyo (JP)

(72) Inventors: Hiroki Kajita, Tokyo (JP); Nobuaki Imanishi, Tokyo (JP); Sadakazu Aiso, Tokyo (JP); Kenichi Nagae, Kanagawa (JP)

(73) Assignees: Canon Kabushiki Kaisha, Tokyo (JP); Luxonus Inc., Kawasaki (JP)

( * ) Notice: Subject to any disclaimer, the term of this patent is extended or adjusted under 35 U.S.C. 154(b) by 802 days.

(21) Appl. No.: 17/180,928

(22) Filed: Feb. 22, 2021

(65) Prior Publication Data

US 2021/0177269 A1    Jun. 17, 2021

Related U.S. Application Data

(63) Continuation of application No. PCT/JP2019/032560, filed on Aug. 21, 2019.

(30) Foreign Application Priority Data

Aug. 24, 2018    (JP) .................. 2018-157794

(51) Int. Cl.
*A61B 5/00*    (2006.01)

(52) U.S. Cl.
CPC .......... *A61B 5/0095* (2013.01); *A61B 5/0033* (2013.01); *A61B 5/418* (2013.01)

(58) Field of Classification Search
CPC ...... A61B 5/0095; A61B 5/0033; A61B 5/418
See application file for complete search history.

(56) References Cited

U.S. PATENT DOCUMENTS 8,384,908 B2 *  2/2013  Sugita ............... G01B 9/02085
                                                  356/479
9,974,440 B2    5/2018  Tsujita
(Continued)

FOREIGN PATENT DOCUMENTS

| JP | 2013-176414 A | 9/2013 |
| JP | 2018-015262 A | 2/2018 |
| WO | 2017/002337 A1 | 1/2017 |

OTHER PUBLICATIONS

Nov. 19, 2019 International Search Report in International Patent Appln. No. PCT/JP2019/032560.

*Primary Examiner* — Baisakhi Roy
(74) *Attorney, Agent, or Firm* — Venable LLP

(57) ABSTRACT

An aspect provides an image processing apparatus processing three-dimensional image data generated based on a photoacoustic wave generated from inside of a subject. The image processing apparatus includes first three-dimensional image acquisition unit for acquiring first three-dimensional image data in which a first region corresponding to a first substance in the subject is extracted from the three-dimensional image data, second three-dimensional image acquisition unit for acquiring second three-dimensional image data in which a second region corresponding to a second substance in the subject is extracted from the three-dimensional image data, first two-dimensional image acquisition unit for acquiring first two-dimensional image data associated with three-dimensional positional information of the first region from the first three-dimensional image data, and second two-dimensional image acquisition unit for acquiring second two-dimensional image data associated with three-dimensional positional information of the second region from the second three-dimensional image data.

19 Claims, 15 Drawing Sheets

(56) References Cited

U.S. PATENT DOCUMENTS

| | | |
|---|---|---|
| 10,765,324 B2 | 9/2020 | Irisawa |
| 2007/0098301 A1* | 5/2007 | Rengakuji .............. H04N 25/48 |
| | | 382/284 |
| 2008/0260227 A1* | 10/2008 | Hayashi ................... A61B 8/06 |
| | | 600/443 |
| 2008/0287967 A1* | 11/2008 | Andreas ............. A61B 17/0057 |
| | | 606/144 |
| 2014/0085448 A1* | 3/2014 | Mitamura ........... A61B 5/0084 |
| | | 348/68 |
| 2014/0371571 A1 | 12/2014 | Tsujita |
| 2015/0005633 A1* | 1/2015 | Kanayama ........... A61B 8/5207 |
| | | 600/438 |
| 2015/0339814 A1* | 11/2015 | Oishi ................... A61B 5/0095 |
| | | 382/131 |
| 2016/0042248 A1* | 2/2016 | Endo ..................... A61B 8/523 |
| | | 382/131 |
| 2016/0135683 A1* | 5/2016 | Yasuno ................ A61B 3/0025 |
| | | 351/246 |
| 2018/0132729 A1 | 5/2018 | Irisawa |
| 2019/0073532 A1* | 3/2019 | Kawase ................. G06V 40/19 |
| 2021/0209799 A1* | 7/2021 | Sugawara ........... H04N 13/246 |

\* cited by examiner

TWO-DIMENSIONAL
LYMPHATIC IMAGE
INDICATING DEPTH INFORMATION
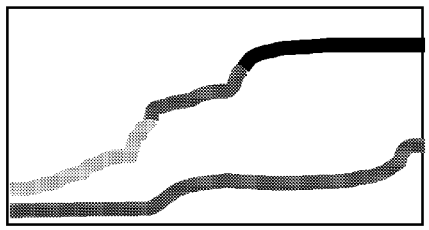
TWO-DIMENSIONAL
BLOOD VESSEL IMAGE
INDICATING DEPTH INFORMATION
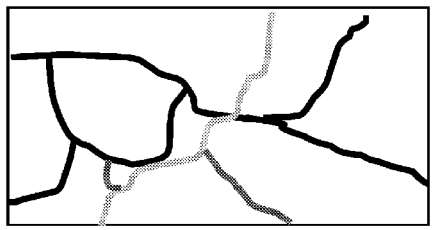
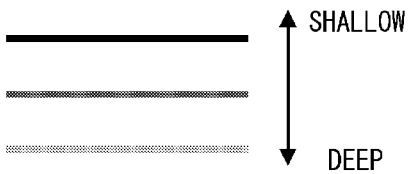
FIG. 8A
FIG. 8B
TWO-DIMENSIONAL
OVERLAPPED AND DISPLAYED IMAGE
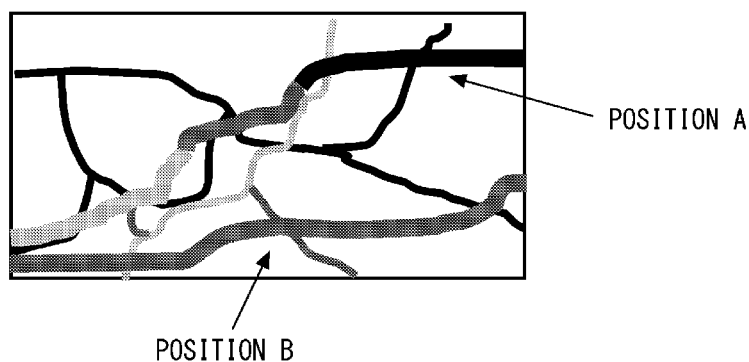
FIG. 8C

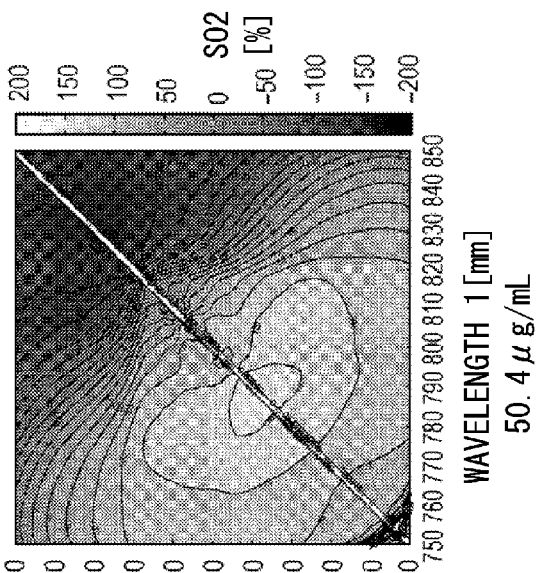
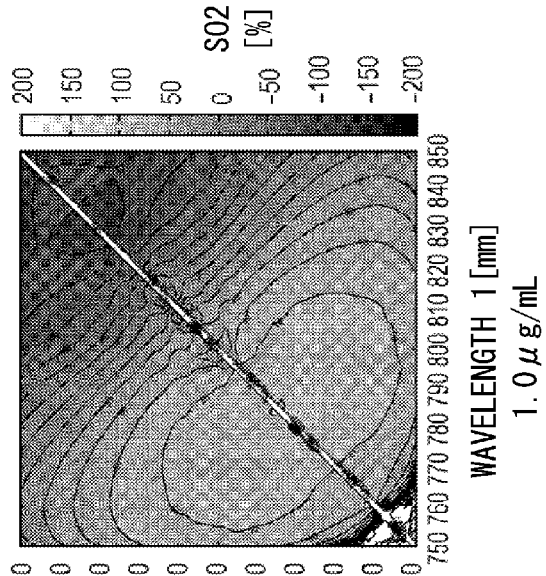
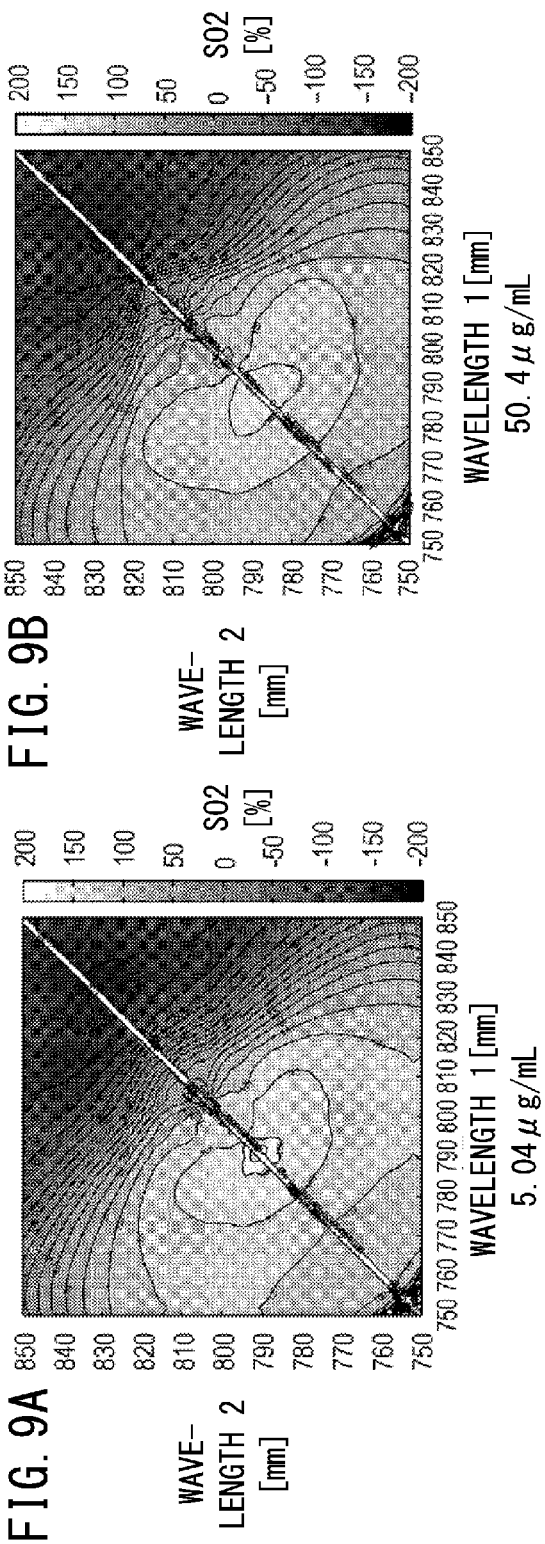
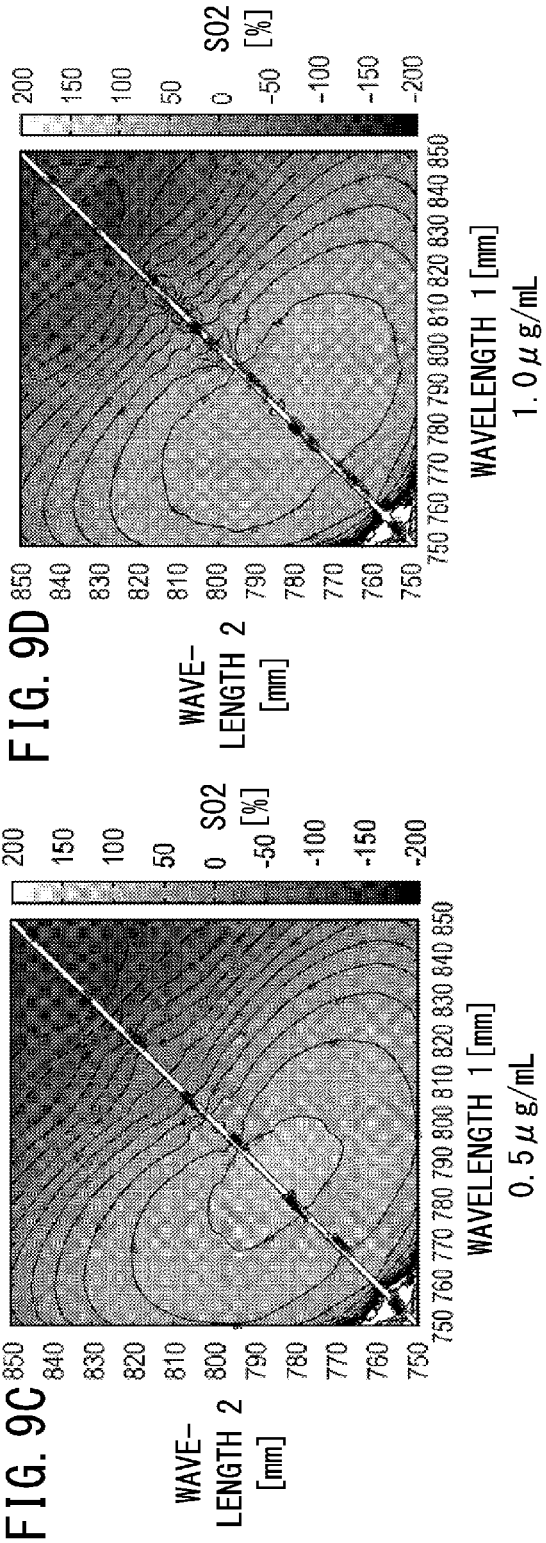
FIG. 9A
FIG. 9B
FIG. 9C
FIG. 9D

IMAGE PROCESSING APPARATUS AND IMAGE PROCESSING METHOD AND NON-TRANSITORY COMPUTER-READABLE MEDIUM

CROSS-REFERENCE TO RELATED APPLICATIONS

This application is a Continuation of International Patent Application No. PCT/JP2019/032560, filed Aug. 21, 2019, which claims the benefit of Japanese Patent Application No. 2018-157794, filed Aug. 24, 2018, which is hereby incorporated by reference herein in their entirety.

BACKGROUND OF THE INVENTION

Field of the Invention

The present invention relates to information processing used in a system generating an image through photoacoustic imaging.

Description of the Related Art

In examination of blood vessels, lymphatic vessels, or the like, photoacoustic imaging in which contrast agents are used (also referred to as "optical ultrasonic imaging") is known. PTL 1 discloses a photoacoustic image generation device in which a contrast agent used for contrast radiography of a lymphatic node, a lymphatic vessel, or the like is set as an evaluation target and the contrast agent absorbs and emits light with a wavelength to generate a photoacoustic wave.

CITATION LIST

Patent Literature

PTL 1 WO 2017/002337

SUMMARY OF THE INVENTION

According to an aspect of the present invention, there is provided an image processing apparatus processing three-dimensional image data generated based on a photoacoustic wave generated from inside of a subject by radiating light to the subject, the image processing apparatus including: first three-dimensional image acquisition unit for acquiring first three-dimensional image data in which a first region corresponding to a first substance in the subject is extracted from the three-dimensional image data; second three-dimensional image acquisition unit for acquiring second three-dimensional image data in which a second region corresponding to a second substance in the subject is extracted from the three-dimensional image data; first two-dimensional image acquisition unit for acquiring first two-dimensional image data associated with three-dimensional positional information of the first region from the first three-dimensional image data; and second two-dimensional image acquisition unit for acquiring second two-dimensional image data associated with three-dimensional positional information of the second region from the second three-dimensional image data. According to another aspect of the present invention, it is provided an image processing method of processing three-dimensional image data generated based on a photoacoustic wave generated from inside of a subject by radiating light to the subject, the method including: a step of acquiring first three-dimensional image data in which a first region corresponding to a first substance in the subject is extracted from the three-dimensional image data; a step of acquiring second three-dimensional image data in which a second region corresponding to a second substance in the subject is extracted from the three-dimensional image data; a step of acquiring first two-dimensional image data associated with three-dimensional positional information of the first region from the first three-dimensional image data; and a step of acquiring second two-dimensional image data associated with three-dimensional positional information of the second region from the second three-dimensional image data.

Further features of the present invention will become apparent from the following description of exemplary embodiments with reference to the attached drawings.

BRIEF DESCRIPTION OF THE DRAWINGS

FIGS. 8A to 8C are schematic diagrams illustrating display of two-dimensional images in which the depth information is reflected;

FIGS. 9A to 9D are contour graphs illustrating calculation values of Expression (1) corresponding to a contrast agent when a combination of wavelengths is changed;

DESCRIPTION OF THE EMBODIMENTS

Figure 1:
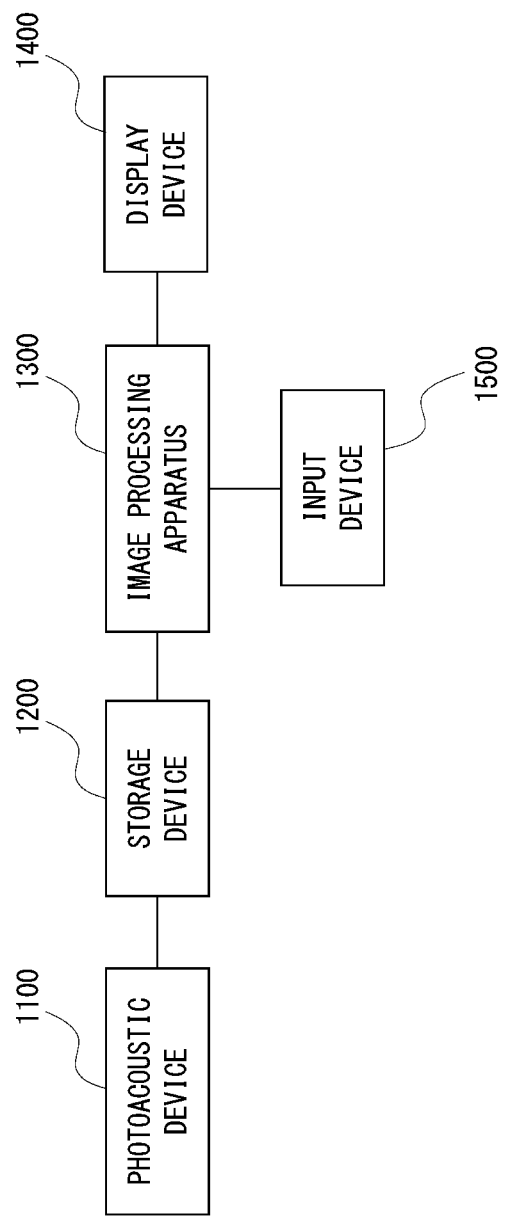
FIG. 1 is a block diagram illustrating a system according to an embodiment of the present invention.

Photoacoustic imaging generally has a problem of a large amount of data.

Accordingly, an objective of the present invention is to provide a technology capable of further reducing an amount of data in photoacoustic imaging than in the related art.

Hereinafter, preferred embodiments of the present invention will be described with reference to the drawings. Here, dimensions, materials, shapes, relative dispositions, and the like of constituent components to be described below are appropriately changed depending on configurations of devices and various conditions applied to the present invention. Accordingly, the scope of the present invention is not limited to the following description.

An absorption amount or an absorption ratio of light energy is reflected in a photoacoustic image obtained by a system according to the present invention. The photoacoustic image indicates a spatial distribution of at least one piece of subject information such as a generated sound pressure (initial sound pressure), optical absorption energy concentration, and an optical absorption coefficient of a photoacoustic wave. The photoacoustic image may be an image indicating a two-dimensional spatial distribution or may be an image (volume data) indicating a three-dimensional spatial distribution. The system according to the embodiment generates a photoacoustic image by imaging a subject into which a contrast agent is introduced. To ascertain a three-dimensional distribution of a contrast radiographic target, the photoacoustic image may indicate an image indicating a two-dimensional spatial distribution or a three-dimensional spatial distribution in a depth direction from a subject surface.

The system according to the present invention can generate a spectral image of a subject using a plurality of photoacoustic images corresponding to a plurality of wavelengths. The spectral image according to the present invention is generated using a photoacoustic signal which corresponds to each of the plurality of wavelengths and is based on a photoacoustic wave generated by radiating light with a plurality of different wavelengths to a subject.

The spectral image may be generated using the photoacoustic signal corresponding to each of the plurality of wavelengths and may indicate concentration of a specific substance in a subject. When an optical absorption coefficient spectrum of a contrast agent which is used is different from an optical absorption coefficient spectrum of the specific substance, an image value of the contrast agent in the spectral image is different from an image value of the specific substance in the spectral image. Accordingly, a region of the contrast agent can be distinguished from a region of the specific substance in accordance with the image value of the spectral image. The specific substance is a substance such as hemoglobin, glucose, collagen, melanin, lipid, and water included in a subject. Even in this case, a contrast agent that has an optical absorption coefficient spectrum different from the optical absorption coefficient spectrum of the specific substance is selected. According to a type of specific substance, a spectral image may be calculated by a different calculation method.

In an embodiment to be described below, a spectral image that has an image value calculated using Calculation Expression (1) for oxygen saturation will be described. The present inventors and the like have found that a calculation value Is(r) considerably deviating from a numerical value range of oxygen saturation of hemoglobin can be obtained when a measured value I(r) of a photoacoustic signal obtained with a contrast agent in which wavelength dependency of an optical absorption coefficient shows a different trend between oxyhemoglobin and deoxyhemoglobin is substituted into Expression (1) for calculating oxygen saturation (an index that has correlation with oxygen saturation may be used) of hemoglobin in blood based on a photoacoustic signal corresponding to each of the plurality of wavelengths. Therefore, when a spectral image that has the calculation value Is(r) as an image value is generated, it is easy to separate (distinguish) a hemoglobin region (a blood vessel region) and a region where the contrast agent is present (for example, a lymphatic vessel region when the contrast agent is introduced to a lymphatic vessel) inside a subject from an image.

$$Is(r) = \frac{\frac{I^{\lambda_2}(r)}{I^{\lambda_1}(r)} \cdot \varepsilon_{Hb}^{\lambda_1} - \varepsilon_{Hb}^{\lambda_2}}{\left(\varepsilon_{HbO}^{\lambda_2} - \varepsilon_{Hb}^{\lambda_2}\right) - \frac{I^{\lambda_2}(r)}{I^{\lambda_1}(r)} \cdot \left(\varepsilon_{HbO}^{\lambda_1} - \varepsilon_{Hb}^{\lambda_1}\right)} \quad \text{EXPRESSION (1)}$$

Here, $I^{\lambda_1}(r)$ is a measured value which is based on a photoacoustic wave generated by radiating light with a first wavelength $\lambda_1$ and $I^{\lambda_2}(r)$ is a measured value which is based on a photoacoustic wave generated by radiating light with a second wavelength $\lambda_2$, $\varepsilon_{Hb}^{\lambda_1}$ is molar absorption coefficient [mm$^{-1}$ mol$^{-1}$] of deoxyhemoglobin corresponding to the first wavelength $\lambda_1$ and $\varepsilon_{Hb}^{\lambda_2}$ is molar absorption coefficient [mm$^{-1}$ mol$^{-1}$] of deoxyhemoglobin corresponding to the second wavelength $\lambda_2$. $\varepsilon_{HbO}^{\lambda_1}$ is molar absorption coefficient [mm$^{-1}$ mol$^{-1}$] of oxyhemoglobin corresponding to the first wavelength $\lambda_1$ and $\varepsilon_{HbO}^{\lambda_2}$ is molar absorption coefficient [mm$^{-1}$ mol$^{-1}$] of oxyhemoglobin corresponding to the second wavelength $\lambda_2$. In addition, r is a position. The measured values $I^{\lambda_1}(r)$ and $I^{\lambda_2}(r)$ may be absorption coefficients $\mu_a^{\lambda_1}(r)$ and $\mu_a^{\lambda_2}(r)$ and may be initial sound pressures $P_0^{\lambda_1}(r)$ and $P_0^{\lambda_2}(r)$.

When the measured value which is based on the photoacoustic wave generated from the hemoglobin presence region (the blood vessel region) is substituted into Expression (1), oxygen saturation (an index that has correlation with oxygen saturation) of hemoglobin can be obtained as the calculation value Is(r). On the other hand, when a measured value which is based on an acoustic wave generated from a region where the contrast agent is present (for example, a lymphatic vessel region) in a subject into which a contrast agent is introduced is substituted into Expression (1), a concentration distribution of a pseudo-contrast agent can be obtained as the calculation value Is(r). Even when the concentration distribution of the contrast agent is calculated, a numerical value of a molar absorption coefficient of hemoglobin in Expression (1) may be used without being changed. In the spectral image that has the image value Is(r) obtained in this way, both a hemoglobin presence region (a blood vessel) and a region where the contrast agent is present (for example, a lymphatic vessel) inside the subject are drawn in a mutually separable (distinguishable) state.

In the embodiment, the image value of the spectral image is calculated using Expression (1) for calculating oxygen saturation. However, when an index other than oxygen saturation is calculated as an image value of the spectral image, a calculation method other than Expression (1) may be used. Since a known index and a known calculation method therefor can be used, detailed description will be omitted.

In the system according to the present invention, the spectral image may be an image indicating a ratio of a first photoacoustic image which is based on a photoacoustic wave generated by radiating light with the first wavelength $\lambda_1$ to a second photoacoustic image which is based on a photoacoustic wave generated by radiating light with the second wavelength $\lambda_2$. That is, the spectral image may be an image which is based on a ratio of the first photoacoustic image which is based on the photoacoustic wave generated by radiating light with the first wavelength $\lambda_1$ to the second photoacoustic image which is based on the photoacoustic wave generated by radiating light with the second wavelength $\lambda_2$. Since an image generated by a modified expression of Expression (1) can be expressed in accordance with a ratio of the first photoacoustic image to the second photoacoustic image, the image can be an image (a spectral image) which is based on the ratio of the first photoacoustic image to the second photoacoustic image.

To ascertain a three-dimensional distribution of a contrast radiographic target, the spectral image may express an image indicating a two-dimensional spatial distribution or a three-dimensional spatial distribution in a depth direction from a subject surface.

Hereinafter, a configuration of the system and an image processing method according to the embodiment will be described.

The system according to the embodiment will be described with reference to FIG. 1. FIG. 1 is a block diagram illustrating a configuration of the system according to the embodiment. The system according to the embodiment includes a photoacoustic device 1100, a storage device 1200, an image processing apparatus 1300, a display device 1400, and an input device 1500. Data may be transmitted and received between the devices in a wired manner or a wireless manner.

The photoacoustic device 1100 generates a photoacoustic image by imaging a subject into which a contrast agent is introduced and outputs the photoacoustic image to the storage device 1200. The photoacoustic device 1100 generates information regarding a specific value corresponding to each of a plurality of positions in a subject using received signal data obtained by receiving a photoacoustic wave generated by radiating light. That is, the photoacoustic device 1100 generates a spatial distribution of specific value information originating from the photoacoustic wave as medical image data (a photoacoustic image).

The storage device 1200 may be a storage medium such as a read-only memory (ROM), a magnetic disk, or a flash memory. The storage device 1200 may be a storage server via a network such as a picture archiving and communication system (PACS).

The image processing apparatus 1300 processes a photoacoustic image stored in the storage device 1200 and information such as supplementary information of the photoacoustic image.

A unit in charge of a calculation function of the image processing apparatus 1300 can be configured by a processor such as a CPU or a graphics processing unit (GPU) or an arithmetic circuit such as a field programmable gate array (FPGA) chip. The units can be configured by a single processor or a single arithmetic circuit and may also be configured from a plurality of processors or a plurality of arithmetic circuits.

The unit in charge of a storage function of the image processing apparatus 1300 can be configured by a non-transitory storage medium such as a read-only memory (ROM), a magnetic disk, or a flash memory. A unit in charge of the storage function may be a volatile medium such as a random access memory (RAM). A storage medium that stores a program is a non-transitory storage medium. The unit in charge of the storage function may be configured by one storage medium or may also be configured by a plurality of storage media.

A unit in charge of a control function of the image processing apparatus 1300 is configured by an arithmetic element such as a CPU. The unit in charge of the control function controls an operation of each configuration of the system. The unit in charge of the control function may receive an instruction signal through any of various operations such as measurement start from an input unit and control each configuration of the system. The unit in charge of the control function may read a program code stored in the computer 150 and control activation of each configuration of the system.

The display device 1400 is a liquid crystal display, an organic electro luminescence (EL) display, or the like. The display device 1400 may display a GUI for operating an image or a device.

The input device 1500 is, for example, an operation console configured by a mouse, a keyboard, or the like which can be operated by a user. The display device 1400 may be configured by a touch panel and the display device 1400 may be used as the input device 1500.

Figure 2:
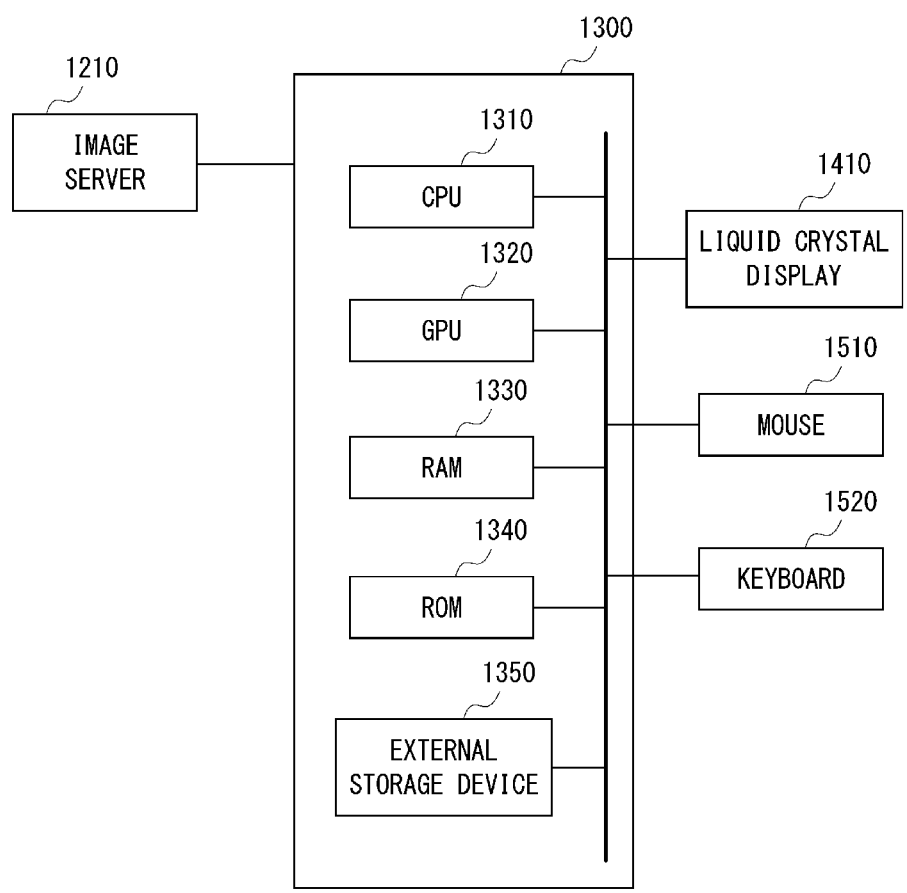
FIG. 2 is a block diagram illustrating a specific example of a configuration of an image processing apparatus and peripherals according to the embodiment of the present invention.

FIG. 2 is a diagram illustrating a specific example of a configuration of the image processing apparatus 1300 according to the embodiment. The image processing apparatus 1300 according to the embodiment includes a CPU 1310, a GPU 1320, a RAM 1330, a ROM 1340, and an external storage device 1350. The liquid crystal display 1410 serving as the display device 1400, the mouse 1510 serving as the input device 1500, and the keyboard 1520 are connected to the image processing apparatus 1300. Further, the image processing apparatus 1300 is connected to an image server 1210 serving as the storage device 1200 such as a picture archiving and communication system (PACS). Thus, image data can be stored on the image server 1210 or the image data on the image server 1210 can be displayed on the liquid crystal display 1410.

Figure 3:
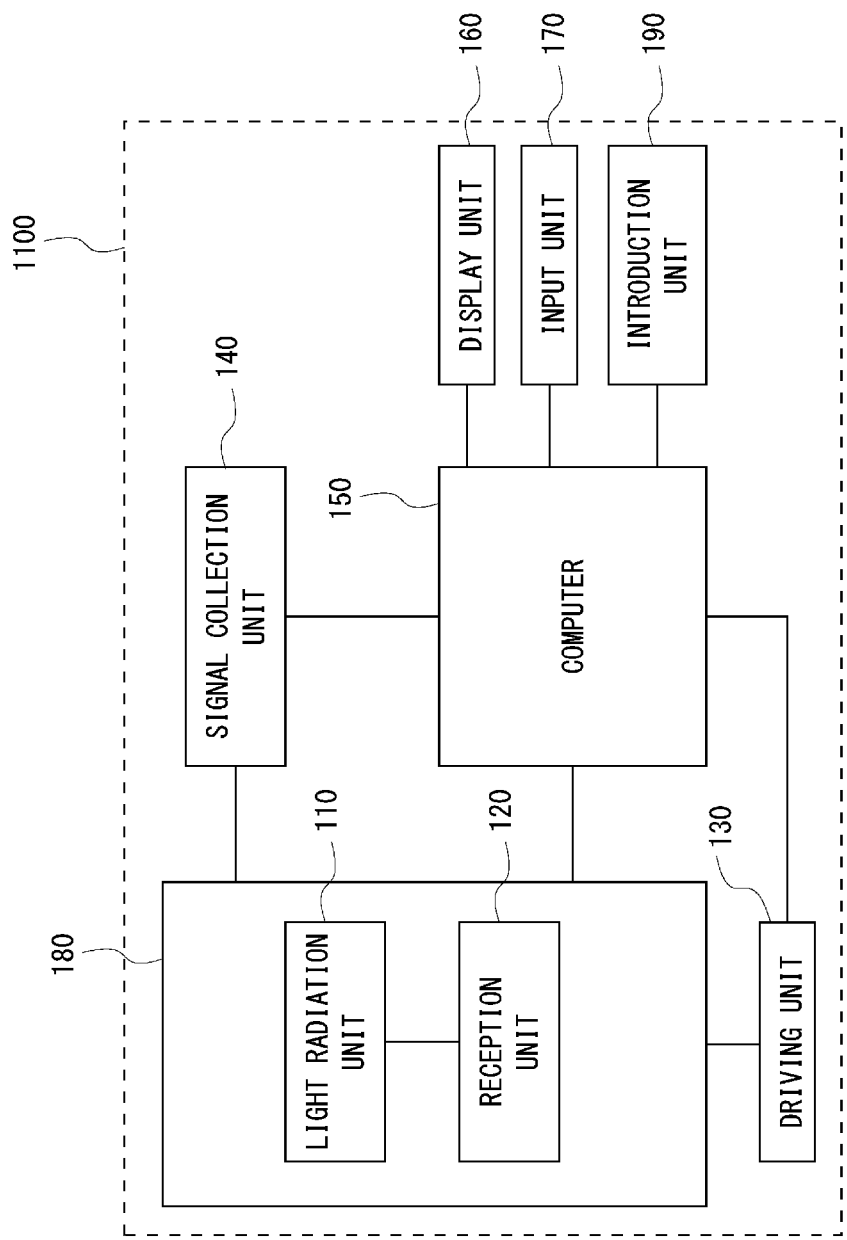
FIG. 3 is a block diagram illustrating details of a photoacoustic device according to the embodiment of the present invention.

Next, a configuration example of the device included in the system according to the embodiment will be described. FIG. 3 is a schematic block diagram illustrating the device included in the system according to the embodiment.

Figure 4:
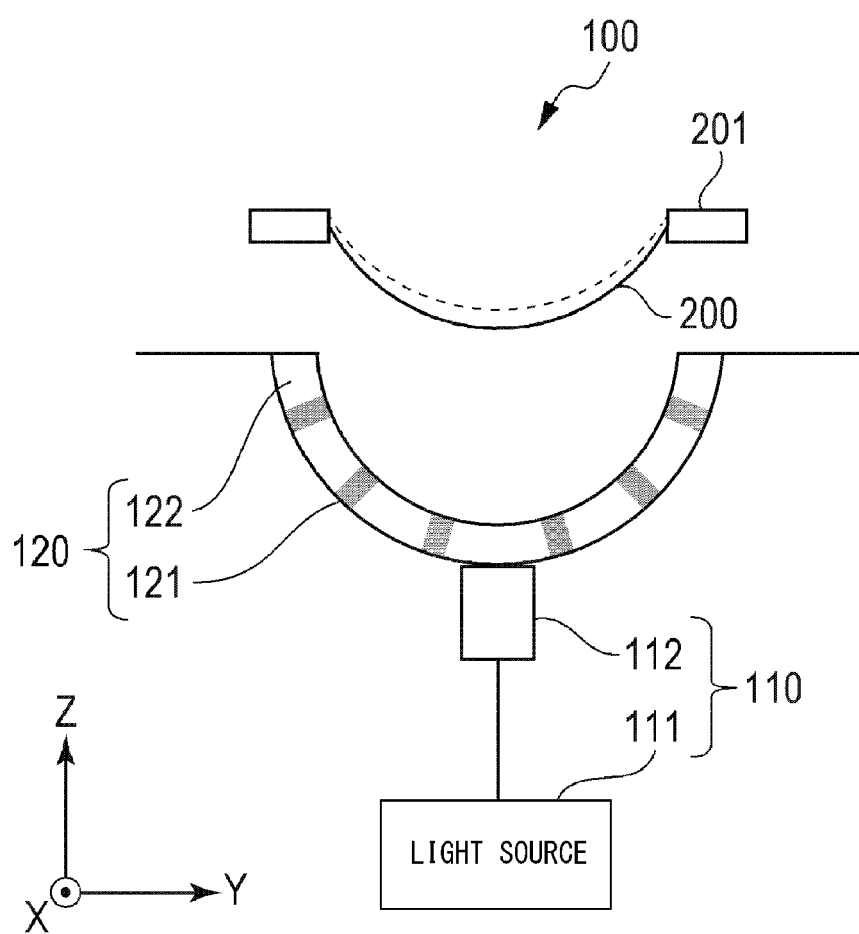
FIG. 4 is a schematic diagram illustrating a probe according to the embodiment of the present invention.

The photoacoustic device 1100 according to the embodiment includes a driving unit 130, a signal collection unit 140, a computer 150, a probe 180, and an introduction unit 190. The probe 180 includes a light radiation unit 110 and a reception unit 120. FIG. 4 is a schematic diagram illustrating the probe 180 according to the embodiment. A measurement target is a subject 100 into which a contrast agent is introduced by the introduction unit 190. The driving unit 130 drives the light radiation unit 110 and the reception unit 120 to perform mechanical scanning. The light radiation unit 110 radiates light to the subject 100, and thus an acoustic wave is generated inside the subject 100. An acoustic wave originating from the light and generated by a photoacoustic effect is also referred to as a photoacoustic wave. The reception unit 120 outputs an electric signal (a photoacoustic signal) as an analog signal by receiving the photoacoustic wave.

The signal collection unit 140 converts the analog signal output from the reception unit 120 into a digital signal and output the digital signal to the computer 150. The computer 150 stores the digital signal output from the signal collection unit 140 as signal data originating from the photoacoustic wave.

The computer 150 generates a photoacoustic image by performing signal processing on the stored digital signal. The computer 150 performs image processing on the obtained photoacoustic image and then outputs the photoacoustic image to the display unit 160. The display unit 160 displays an image which is based on the photoacoustic image. Based on a storage instruction from the user or the computer 150, the displayed image is stored in a memory in the computer 150 or the storage device 1200 such as a data management system connected to a modality and a network.

The computer 150 also performs driving control of the configuration included in the photoacoustic device. The display unit 160 may display a GUI or the like in addition to an image generated by the computer 150. The input unit 170 is configured so that the user can input information. The user can execute starting or ending of measurement, an instruction to store a generated image, and the like using the input unit 170.

Hereinafter, details of each configuration of the photoacoustic device 1100 according to the embodiment will be described.

(Light Radiation Unit 110)

The light radiation unit 110 includes a light source 111 that emits light and an optical system 112 that guides the light emitted from the light source 111 to the subject 100. The light includes pulsed light such as a so-called rectangular wave and triangular wave.

A pulsed width of the light emitted from the light source 111 is preferably a pulsed width of not more than 100 ns in consideration of a heat containment condition and a stress containment condition. A wavelength of light may be in the range of about 400 nm to 1600 nm. When a blood vessel is imaged with a high resolution, a wavelength (which is at least 400 nm and not more than 700 nm) with large absorption in a blood vessel may be used. When a deep part of a living body is imaged, light with a wavelength (which is at least 700 nm and not more than 1100 nm) that typically absorbs less light in a background tissue (water, lipid, or the like) of a living body may be used.

The light source 111 is, a laser, a light-emitting diode, or the like. When measurement is performed using light with a plurality of wavelengths, a light source capable of changing the wavelength may be used. When light with a plurality of wavelengths is radiated to the subject, a plurality of light sources generating light with different wavelengths can also be prepared and light is alternately radiated from the light sources. Even when a plurality of light sources are used, the light sources are collectively expressed as the light source. As the laser, any of various lasers such as a solid-state laser, a gas laser, a dye laser, and a semiconductor laser can be used. For example, a pulsed laser such as a Nd:YAG laser or an alexandrite laser may be used. An optical parametric oscillators (OPO) laser or a Ti:sa laser using a Nd:YAG laser light as exciting light may be used as the light source. A flash lamp or a light-emitting diode may be used as the light source 111. A microwave source may be used as the light source 111.

An optical element such as a lens, a mirror, or an optical fiber can be used in the optical system 112. When a breast or the like is used as the subject 100, a light emission unit of the optical system may be configured by a diffusion plate or the like diffusing light in order to expand and radiate a beam diameter of pulsed light. On the other hand, in a photoacoustic microscopy, the light emission unit of the optical system 112 may be configured by a lens or the like to focus and radiate a beam to raise a resolution.

The light radiation unit 110 may radiate light directly to the subject 100 from the light source 111 without including the optical system 112.

(Reception Unit 120)

The reception unit 120 includes a transducer 121 that outputs an electric signal by receiving an acoustic wave and a supporter 122 that supports the transducer 121. The transducer 121 may be a transmitter that transmits acoustic waves. A transducer serving as a receiver and a transducer serving as a transmitter may be a single (common) transducer or may be configured separately.

As a member included in the transducer 121, a piezoelectric ceramic material typified by lead zirconate titanate (PZT), a polymer piezoelectric film material typified by polyvinylidene difluoride (PVDF), or the like can be used. An element other than a piezoelectric element may be used. For example, a transducer using capacitive micro-machine ultrasonic transducers (CMUT) can be used. Any transducer may be adopted as long as the transducer can output an electric signal by receiving acoustic waves. A signal obtained by the transducer is a time-resolved signal. That is, an amplitude of a signal obtained by the transducer indicates a value (for example, a value proportional to a sound pressure) which is based on a sound pressure received by the transducer at each time.

A frequency component included in the photoacoustic wave is typically in the range of 100 KHz to 100 MHz and the transducer 121 capable of detecting such a frequency may be adopted.

The supporter 122 may be formed of a metal material that has high mechanical strength. To cause much radiated light to be incident on a subject, mirror processing or finishing for scattering light may be performed on the surface of the supporter 122 on the side of the subject 100. In the embodiment, the supporter 122 is formed with a hemispherical shell-like shape and configured to be able to support the plurality of transducers 121 on the hemispherical shell. In this case, an orientation axis of the transducer 121 disposed in the supporter 122 gather near the center of curvature of the hemisphere. Image quality near the center of curvature increases at the time of imaging using signals output from the plurality of transducers 121. The supporter 122 may have any configuration as long as the supporter 122 can support the transducers 121. The supporter 122 may be disposed by arranging a plurality of transducers on a plane or a curve called a 1D array, a 1.5D array, a 1.75D array, or a 2D array. The plurality of transducers 121 correspond to a plurality of receivers.

The supporter 122 may function as a container that stores an acoustic matching material. That is, the supporter 122 may be a container for disposing the acoustic matching material between the transducer 121 and the subject 100.

The reception unit 120 may have an amplifier that amplifies time-series analog signals output from the transducers 121. The reception unit 120 may have an A/D converter that converts the time-series analog signals output from the transducers 121 into time-series digital signals. That is, the reception unit 120 may include the signal collection unit 140 to be described below.

A space between the reception unit 120 and the subject 100 is filled with a medium that can transfer photoacoustic waves. This medium is a material through which an acoustic wave can propagate, which has a matching acoustic feature on an interface with the subject 100 or the transducer 121, and which has high transmittance of the photoacoustic wave as much as possible. For example, this medium is water, an ultrasonic gel, or the like.

FIG. 4 is a side view illustrating the probe 180. The probe 180 according to the embodiment includes the reception unit 120 in which the plurality of transducers 121 are disposed three-dimensionally on the supporter 122 that has a hemispheric shape with an opening. A light emission unit of the optical system 112 is disposed on the bottom of the supporter 122.

In the embodiment, as illustrated in FIG. 4, the subject 100 comes into contact with a retention unit 200, and thus the shape of the subject 100 is retained.

A space between the reception unit 120 and the retention unit 200 is filled with a medium that can transfer a photoacoustic wave. This medium is a material through which a photoacoustic wave can propagate, which has a matching acoustic feature on an interface with the subject 100 or the transducer 121, and which has high transmittance of the photoacoustic wave as much as possible. For example, this medium is water, an ultrasonic gel, or the like.

The retention unit 200 serving as a retainer retains the shape of the subject 100 during measurement. When the retention unit 200 retains the subject 100, a motion of the subject 100 can be inhibited and the position of the subject 100 can be kept inside the retention unit 200. As a material of the retention unit 200, a resin material such as polycarbonate, polyethylene, or polyethylene terephthalate can be used.

The retention unit 200 is mounted on a mounting unit 201. The mounting unit 201 may be configured such that a plurality of types of retention units 200 can be exchanged in accordance with the size of a subject. For example, the mounting unit 201 may be configured such that the retention unit can be exchanged with a retention unit of which a radius of curvature or a center of curvature, or the like is different.

(Driving Unit 130)

The driving unit 130 changes relative positions of the subject 100 and the reception unit 120. The driving unit 130 includes a motor such as a stepping motor that generates a driving force, a driving mechanism that transmits the driving force, and a position sensor that detects positional information of the reception unit 120. The driving mechanism is a lead screw mechanism, a link mechanism, a gear mechanism, and a hydraulic mechanism, or the like. The position sensor is a potentiometer such as an encoder, a variable resistor, a linear scale, a magnetic sensor, an infrared sensor, or an ultrasonic sensor.

The driving unit 130 may change the relative positions of the subject 100 and the reception unit 120 one-dimensionally or three-dimensionally without being limited to the change in the relative positions in the XY directions (two-dimensionally).

The driving unit 130 may fix the reception unit 120 and move the subject 100 as long as the relative positions of the subject 100 and the reception unit 120 can be changed. When the subject 100 is moved, the subject 100 is considered to be moved by moving the retention unit that retains the subject 100. Both the subject 100 and the reception unit 120 may be moved.

The driving unit 130 may continuously move the relative positions or may move the relative positions in a step-and-repeat manner. The driving unit 130 may be an electric stage moving the relative positions in a programmed trajectory or may be a manual stage.

In the embodiment, the driving unit 130 performs scanning by simultaneously driving the light radiation unit 110 and the reception unit 120, but may drive only the light radiation unit 110 or may drive only the reception unit 120.

When the probe 180 is a small type of probe which includes a gripping portion, the photoacoustic device 1100 may not include the driving unit 130.

(Signal Collection Unit 140)

The signal collection unit 140 includes an amplifier that amplifies an electric signal which is an analog signal output from the transducer 121 and an A/D converter that converts the analog signal output from the amplifier into a digital signal. The digital signal output from the signal collection unit 140 is stored in the computer 150. The signal collection unit 140 is also called a data acquisition system (DAS). An electric signal in the present specification has a concept that also includes both an analog signal and a digital signal. A light detection sensor such as a photodiode may detect light emitted from the light radiation unit 110 and the signal collection unit 140 may start the foregoing process by synchronizing a detection result with a trigger.

(Computer 150)

The computer 150 serving as an information processing device is configured by hardware similar to that of the image processing apparatus 1300. That is, a unit in charge of an arithmetic function of the computer 150 can be configured by a processor such as a CPU or a graphics processing unit (GPU) or an arithmetic circuit such as a field programmable gate array (FPGA). The units can be configured by a single processor or a single arithmetic circuit and may also be configured from a plurality of processors or a plurality of arithmetic circuits.

The unit in charge of a storage function of the computer 150 may be a volatile medium such as a random access memory (RAM). A storage medium that stores a program is a non-transitory storage medium. The unit in charge of the storage function of the computer 150 may be configured by one storage medium or may also be configured by a plurality of storage media.

The unit in charge of a control function of the computer 150 is configured by an arithmetic element such as a CPU. The unit in charge of the control function of the computer 150 controls an operation of each configuration of the photoacoustic device. The unit in charge of the control function of the computer 150 may receive an instruction signal through any of various operations such as measurement start from the input unit 170 and control each configuration of the photoacoustic device. The unit in charge of the control function of the computer 150 may read a program code stored in the unit in charge of the storage function and control activation of each configuration of the photoacoustic device. That is, the computer 150 can function as a control device of the system according to the embodiment.

The computer 150 and the image processing apparatus 1300 may be configured by the same hardware. Single hardware may be in charge of the functions of both the computer 150 and the image processing apparatus 1300. That is, the computer 150 may be in charge of the function of the image processing apparatus 1300. The image processing apparatus 1300 may be in charge of the function of the computer 150 serving as an information processing device.

(Display Unit 160)

The display unit 160 is a liquid crystal display, an organic electro luminescence (EL) display, or the like. The display unit 160 may display a GUI for operating an image or a device.

The display unit 160 and the display device 1400 may be the same display. That is, a single display may be in charge of the functions of both the display unit 160 and the display device 1400.

(Input Unit 170)

The input unit 170 is, for example, an operation console configured by a mouse, a keyboard, or the like which can be operated by the user. The display unit 160 may be configured by a touch panel and the display unit 160 may be used as the input unit 170.

The input unit 170 and the input device 1500 may be the same device. That is, a single device may be in charge of the functions of both the input unit 170 and the input device 1500.

(Introduction Unit 190)

The introduction unit 190 is configured to be able to introduce a contrast agent into the inside of the subject 100 from the outside of the subject 100. For example, the introduction unit 190 can include a container for the contrast agent and an injection needle pierced into a subject. However, the present invention is not limited thereto and the introduction unit 190 may be any of various units that can introduce a contrast agent into the subject 100. In this case, the introduction unit 190 may be, for example, a known injection system or injector. The computer 150 serving as a control device may introduce the contrast agent into the subject 100 by controlling an operation of the introduction unit 190. The user may introduce the contrast agent into the subject 100 by operating the introduction unit 190.

(Subject 100)

The subject 100 that is not included in the system will be described below. The system according to the embodiment can be used, for example, in order to diagnose a malignant tumor, a vascular disease, or the like of a human being or an animal or observe a progress of a chemical treatment. Accordingly, as the subject 100, a diagnostic target part such as a living body, specifically, a breast, each organ, a vascular plexus, a head part, a neck part, an abdomen part, or four limbs such as fingers and toes of a human body or an animal, is assumed. For example, when a human body is a measurement target, an optical absorber target is a new blood vessel or the like formed near oxyhemoglobins or deoxyhemoglobins or a blood vessel or a tumor that contains many oxyhemoglobins or deoxyhemoglobins. The optical absorber target may be plaque or the like of a carotid wall or may be melanin, collagen, lipid, or the like contained in skin. Further, a contrast agent introduced into the subject 100 can be an optical absorber. A contrast agent used for photoacoustic imaging is a pigment such as indocyanine green (ICG) or methylene blue (MB), a gold fine particle, and a mixture thereof, or a substance accumulated or chemically modified from them and introduced from the outside. The subject 100 may be the subject 100 which is a phantom resembling a living body.

The configurations of the photoacoustic device may be configured as separate devices or may be configured as a single integrated device. The configurations of the photoacoustic device may be configured as a single device in which a configuration of at least a part of the photoacoustic device is integrated.

The devices included in the system according to the embodiment may be configured as separate hardware or all the devices may be configured with single hardware. The functions of the system according to the embodiment may be configured with any hardware.

Figure 5:
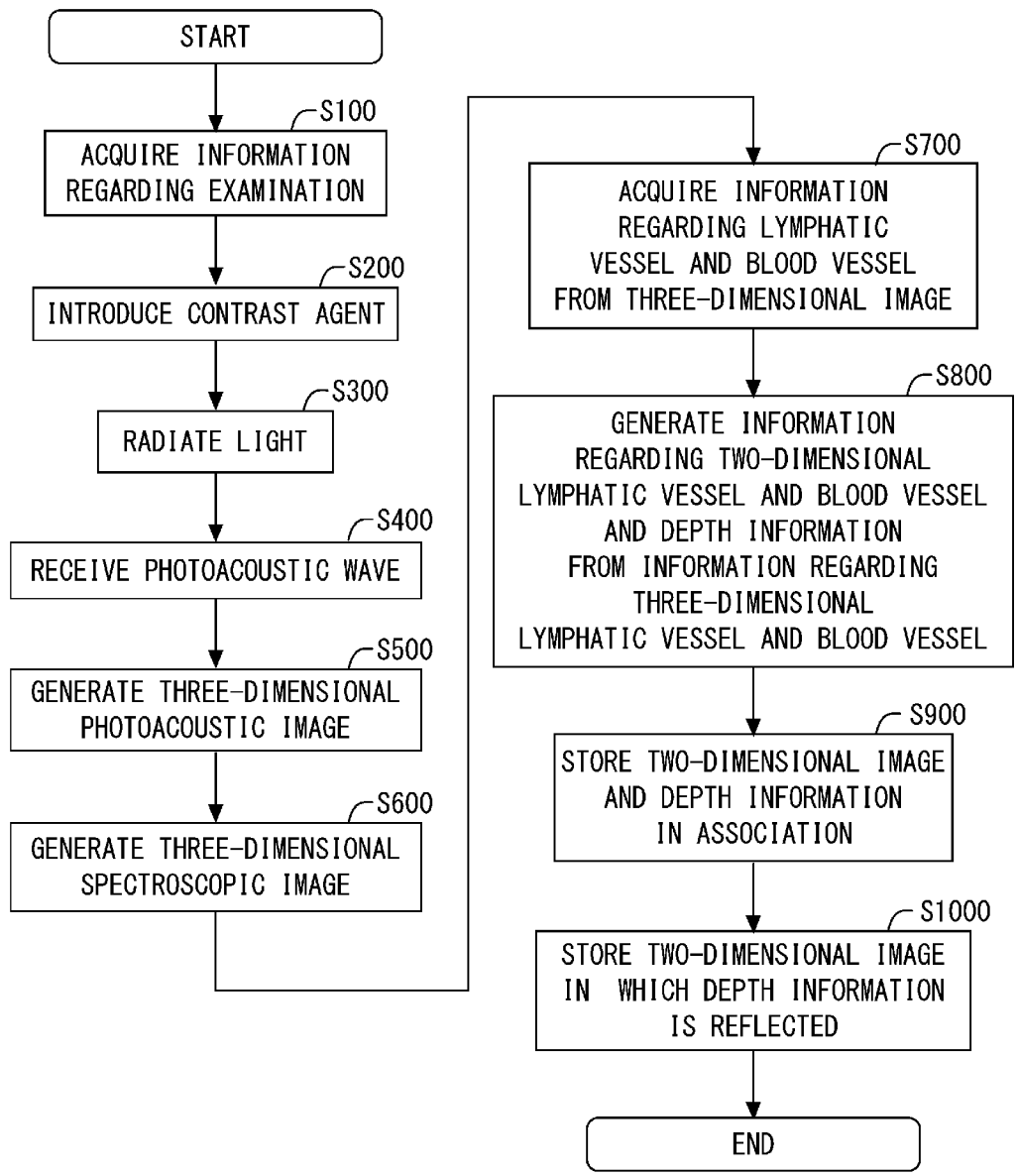
FIG. 5 is a flowchart illustrating an image processing method according to the embodiment of the present invention.

Next, an image generation method according to the embodiment will be described with reference to the flowchart illustrated in FIG. 5. The flowchart illustrated in FIG. 5 includes a step indicating an operation of the system according to the embodiment and also includes a step indicating an operation of a user such as a physician.

(S100: Step of Acquiring Information Regarding Examination)

The computer 150 of the photoacoustic device 1100 acquires information regarding examination. For example, the computer 150 acquires examination order information transmitted from an information system in hospital, such as a hospital information system (HIS) or a radiology information system (RIS). The examination order information includes a type of modality used for the examination or information regarding a contrast agent or the like used for the examination. When the modality is photoacoustic imaging, the examination order information includes information regarding light to be radiated. In a main embodiment of the present invention, subject information is acquired by radiating light with at least a single wavelength to the subject. When spectral information is acquired, subject information obtained by radiating light with each of a plurality of wavelengths to the subject is acquired. Information regarding light includes a pulse length, a repetition frequency, and intensity of light with each wavelength.

When a plurality of wavelengths are used and a spectral image that has an image value in accordance with Expression (1) is generated, the image value in accordance with actual oxygen saturation is calculated in a blood vessel region in the spectral image in the setting of the wavelengths. In a region in which there is a contrast agent in the spectral image (hereinafter also referred to as a contrast agent region), on the other hand, it is preferable to consider a wavelength to be used or a large change in an image value by an absorption coefficient spectrum of the contrast agent. That is, in order to easily ascertain a three-dimensional distribution of the contrast agent, it is preferable to use a wavelength in which the image value of the contrast agent region in the spectral image is a value which can be distinguished from the image value of the blood vessel region. Specifically, when an image is generated as a spectral image using Expression (1), it is preferable to use two wavelengths at which a calculated value of Expression (1) corresponding to the contrast agent in the spectral image is less than 60% (for example, becomes a negative value) or greater than 100% by using arteriovenous oxygen saturation which is mostly in the range of 60% to 100% displayed by percentage. Based on information regarding the contrast agent, the computer 150 may determine two wavelengths at which signs of the image value of a region corresponding to the contrast agent in the spectral image and an image value of the other region are reversed. For example, when ICG is used as the contrast agent, it is possible to satisfactorily identify the contrast agent region from the blood vessel region by selecting two wavelengths, a wavelength which is at least 700 nm and not more than 820 nm and a wavelength which is at least 820 nm and not more than 1020 nm, and generating a spectral image by Expression (1).

The user may use the input unit 170 to give an instruction for a type of modality used for examination, information regarding light when the modality is photoacoustic imaging, a type of contrast agent used for the examination, or concentration of the contrast agent. In this case, the computer 150 can acquire examination information via the input unit 170. The computer 150 may store information regarding a plurality of contrast agents in advance and acquire information regarding a contrast agent set as default among them.

Figure 12:
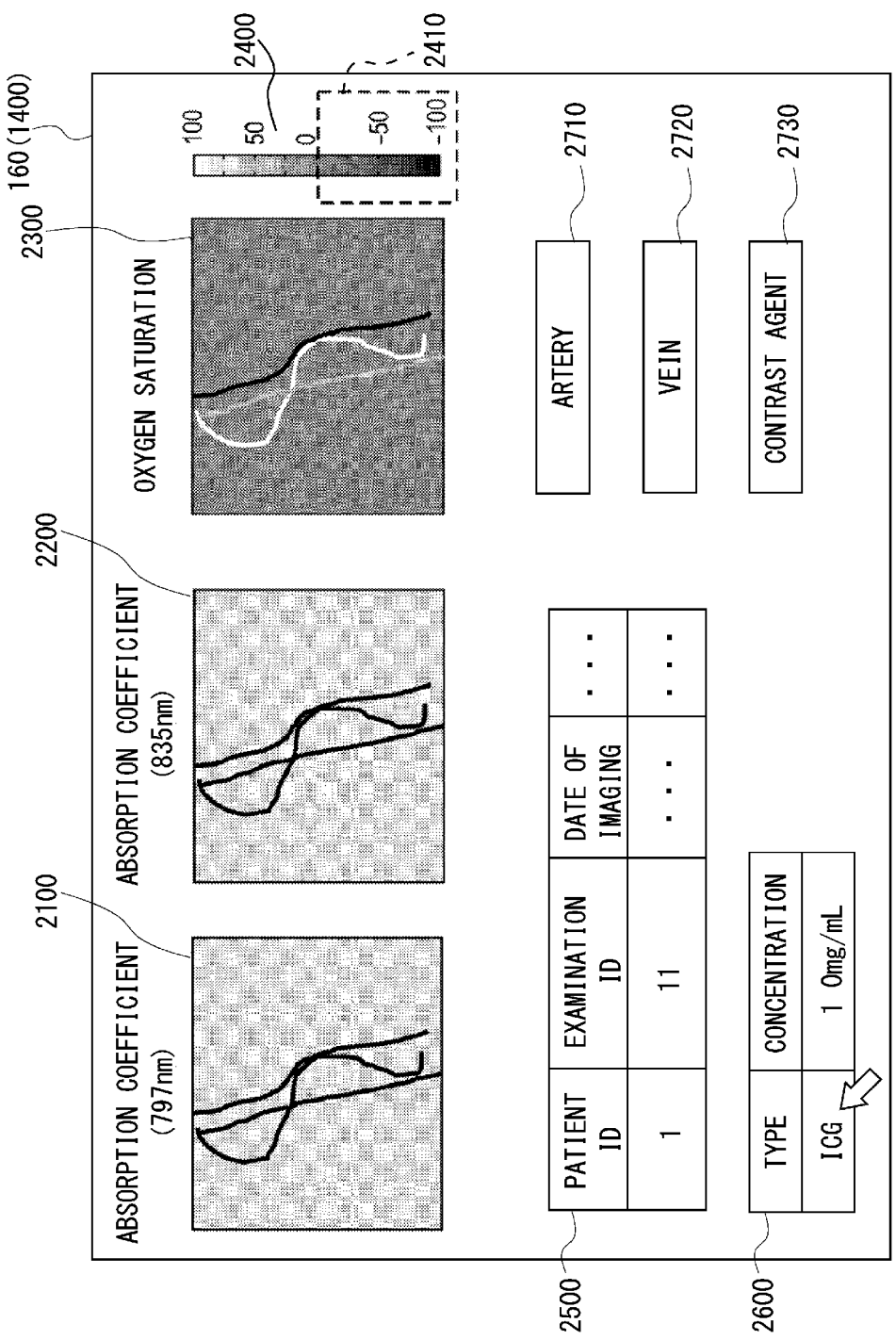
FIG. 12 is a diagram illustrating a GUI according to the embodiment of the present invention.

FIG. 12 is a diagram illustrating an example of a GUI displayed on the display unit 160. In an item 2500 of the GUI, examination order information such as a patient ID, an examination ID, and a date of imaging is displayed. The item 2500 may have a display function of displaying the examination order information acquired from an external device such as an HIS or a RIS or an input function by which the user can inputs the examination order information using the input unit 170. In an item 2600 of the GUI, information regarding the contrast agent, such as a type of contrast agent or concentration of the contrast agent, is displayed. The item 2600 may have a display function of displaying information regarding the contrast agent acquired from an external device such as an HIS or a RIS or an input function by which the user can inputs the information regarding the contrast agent using the input unit 170. In the item 2600, the information regarding the contrast agent, such as the concentration or type of contrast agent can also be input in a pull-down manner in a plurality of options. The GUI illustrated in FIG. 12 may be displayed on the display device 1400.

When an instruction to input the information regarding the contrast agent is not received from the user, the image processing apparatus 1300 may acquire the information regarding the contrast agent set as default from the information regarding the plurality of contrast agents. In the embodiment, a case in which ICG is set as a type of contrast agent and 1.0 mg/mL is set as concentration of the contrast agent as default will be described. In the embodiment, in the item 2600 of the GUI, the concentration and type of contrast agent set as default are displayed, but the information regarding the contrast agent may not be set as default. In this case, on an initial screen, the information regarding the contrast agent may not be displayed in the item 2600 of the GUI.

(S200: Step of Introducing Contrast Agent)

The introduction unit 190 introduces the contrast agent into the subject. When the user uses the introduction unit 190 to introduce the contrast agent into the subject, the user may operate the input unit 170 to transmit a signal indicating the introduction of the contrast agent from the input unit 170 to the computer 150 serving as a control device. The signal indicating that the introduction unit 190 introduces the contrast agent into the subject 100 may be transmitted to the computer 150. The contrast agent may be administered into the subject without using the introduction unit 190. For example, the contrast agent may be administered when a living body serving as a subject sucks a sprayed contrast agent.

After the contrast agent is introduced, a subsequent process may be performed at intervals until the contrast agent spreads as a contrast radiographic target inside the subject 100.

Here, a spectral image obtained by imaging the living body into which the ICG has been introduced using the photoacoustic device will be described. FIGS. 13 to 15 are diagrams illustrating spectral images captured and obtained when the ICG is introduced changing concentration. In all the imaging, the ICG of 0.1 mL was introduced into one location of a subcutaneous or intradermal part of a hand or a foot. Since the ICG introduced into the subcutaneous or intradermal part is received selectively in a lymphatic vessel, a lumen of the lymphatic vessel is contrasted. In all the imaging, the spectral images were captured within 5 minutes to 60 minutes from the introduction of the ICG. All the spectral images are generated from the photoacoustic images obtained by radiating light with a wavelength of 797 nm and light with a wavelength of 835 nm to the living body.

Figure 13B:
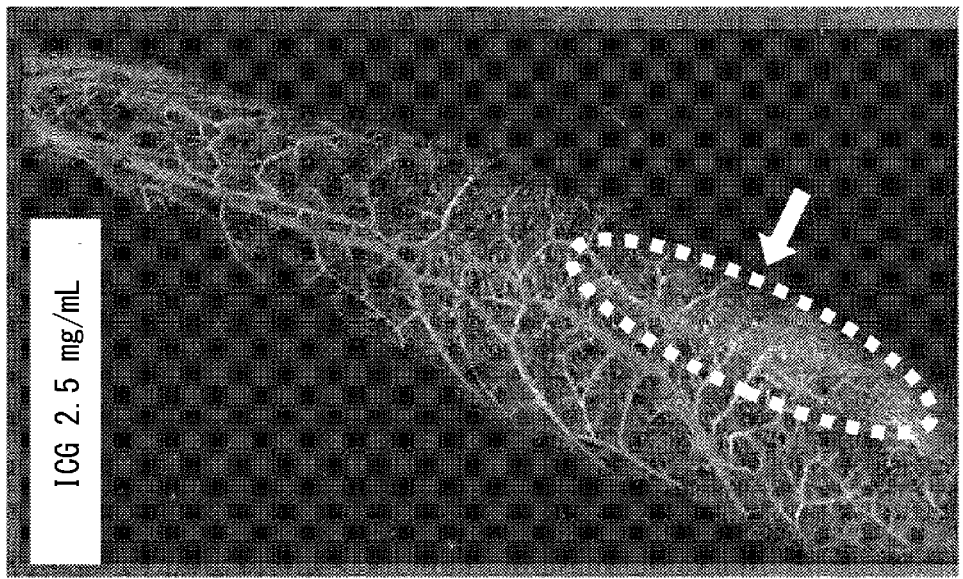
FIGS. 13A and 13B are diagrams illustrating spectral images of a stretched right front arm side when concentration of ICG is changed.
Figure 13A:
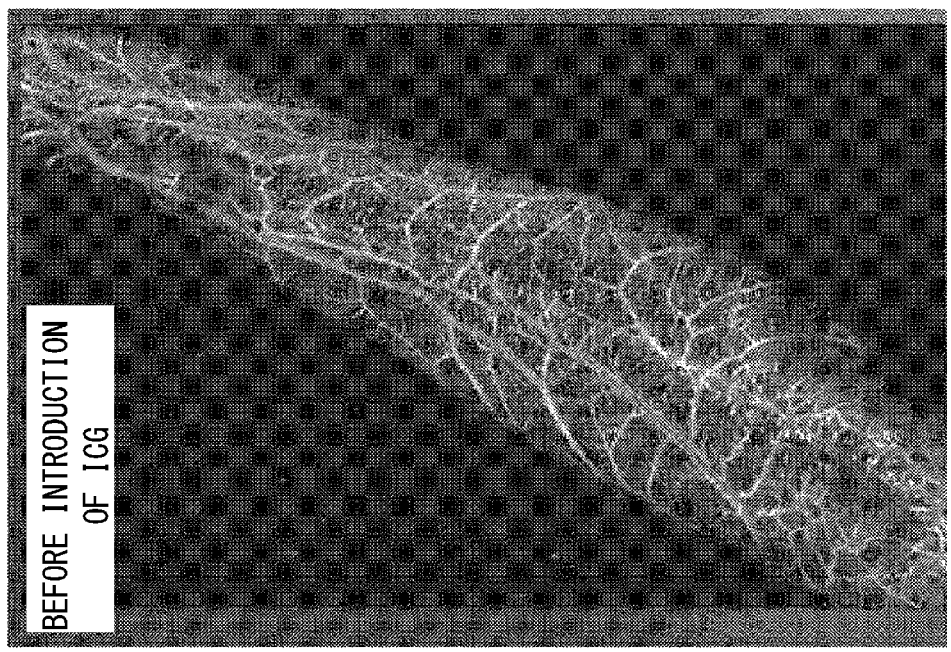

FIG. 13A illustrates a spectral image of a stretched right front arm side when the ICG was not introduced. On the other hand, FIG. 13B illustrates a spectral image of the stretched right front arm side when the ICG with concentration of 2.5 mg/mL was introduced. A lymphatic vessel is drawn in a region indicated by a dotted line and an arrow in FIG. 13B.

Figure 14B:
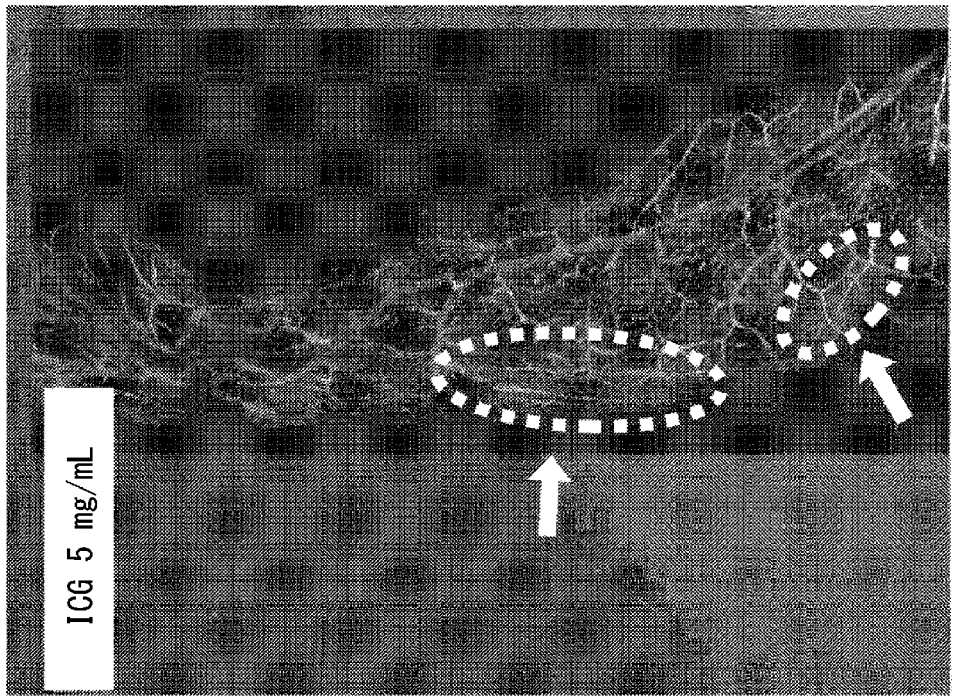
FIGS. 14A and 14B are diagrams illustrating spectral images of stretched left front arm side when concentration of ICG is changed.
Figure 14A:
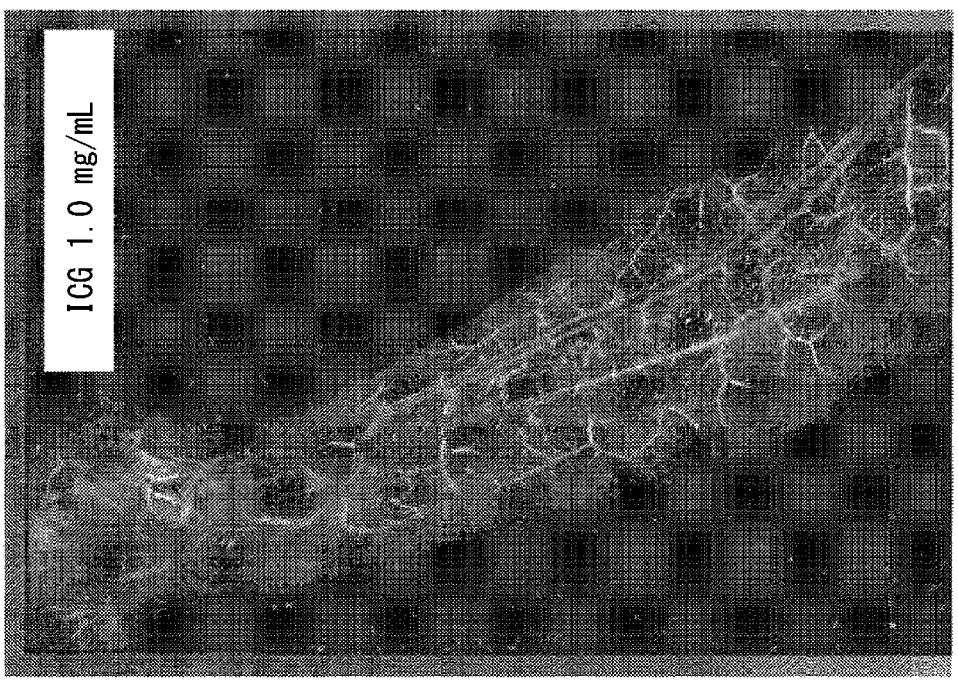

FIG. 14A illustrates a spectral image of a stretched left front arm side when the ICG with concentration of 1.0 mg/mL was introduced. FIG. 14B illustrates a spectral image of a stretched left front arm side when the ICG with concentration of 5.0 mg/mL was introduced. A lymphatic vessel is drawn in a region indicated by a dotted line and an arrow in FIG. 14B.

Figure 15B:
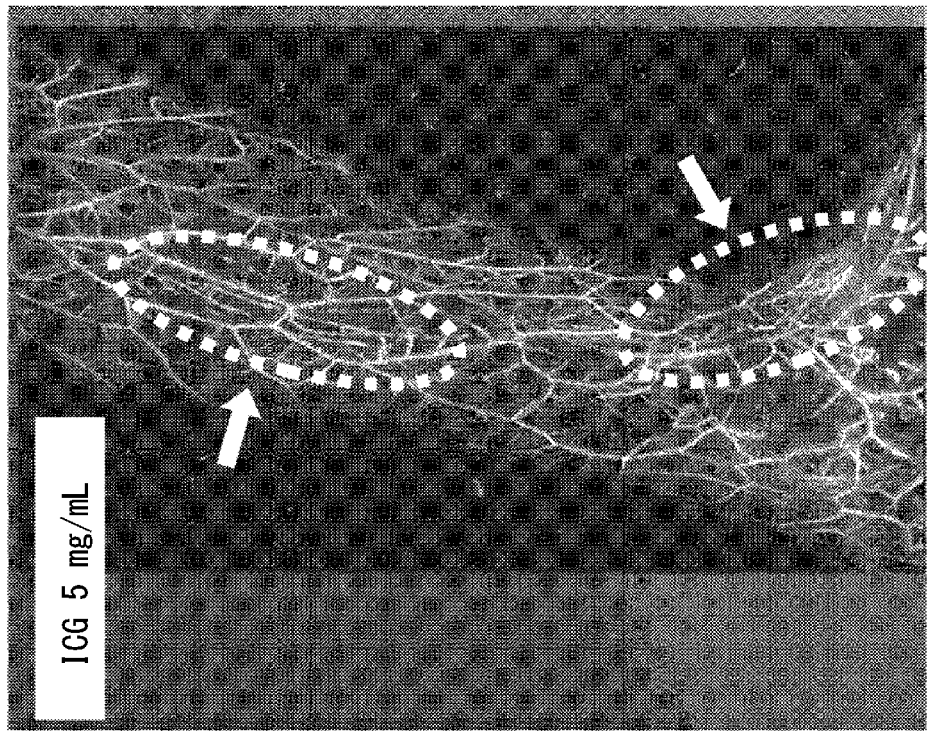
FIGS. 15A and 15B are diagrams illustrating spectral images of an inner lower right thigh side and an inner lower left thigh side when concentration of ICG is changed.
Figure 15A:
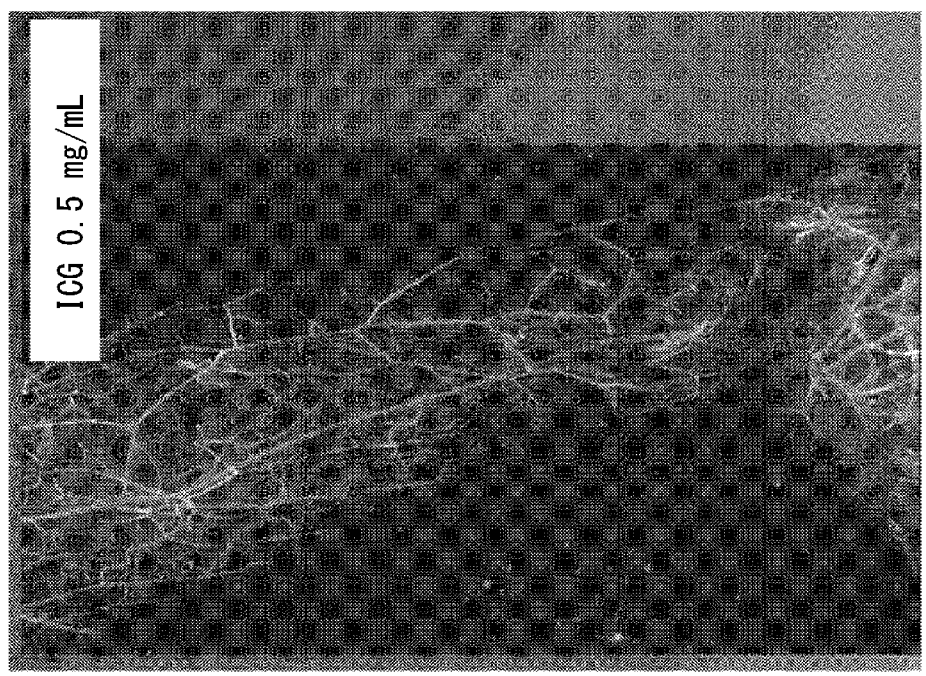

FIG. 15A illustrates a spectral image of an inner lower right thigh side when the ICG with concentration of 0.5 mg/mL was introduced. FIG. 15B illustrates a spectral image of an inner lower left thigh side when the ICG with concentration of 5.0 mg/mL was introduced. A lymphatic vessel is drawn in a region indicated by a dotted line and an arrow in FIG. 15B.

From the spectral images illustrated in FIGS. 13 to 15, it can be understood that visibility of the lymphatic vessels in the spectral images is improved when the concentration of the ICG is increased. From FIGS. 13 to 15, it can be understood that the lymphatic vessels can be drawn satisfactorily when the concentration of the ICG is at least 2.5 mg/mL. That is, when the concentration of the ICG is at least 2.5 mg/mL, the lymphatic vessel on lines can be clearly viewed. Therefore, when the ICG is adopted as the contrast agent, the concentration of the ICG may be at least 2.5 mg/mL. The concentration of the ICG may be greater than 5.0 mg/mL in consideration of dilution of the ICG in the living body. Here, in view of solubility of diagnogreen, it is difficult to solve the ICG with a concentration of at least 10.0 mg/mL in a water solution.

From the above, the concentration of the ICG introduced into the living body may be at least 2.5 mg/mL and not more than 10.0 mg/mL and is preferably at least 5.0 mg/mL and not more than 10.0 mg/mL.

Accordingly, the computer 150 may selectively receive an instruction indicating the concentration of the ICG within the foregoing numerical value range from the user when the ICG is input as the type of contrast agent in the item 2600 of the GUI illustrated in FIG. 12. That is, in this case, the computer 150 may not receive an instruction indicating concentration of the ICG outside of the foregoing numerical value range from the user. Accordingly, when the information indicating that the type of contrast agent is the ICG is acquired, the computer 150 may not receive an instruction indicating the concentration of the ICG less than 2.5 mg/mL or greater than 10.0 mg/mL from the user. When the information indicating that the type of contrast agent is the ICG is acquired, the computer 150 may not receive an instruction indicating the concentration of the ICG less than 5.0 mg/mL or greater than 10.0 mg/mL from the user.

The computer 150 may configure the GUI so that the user cannot give an instruction for concentration of the ICG outside of the foregoing numerical value range on the GUI. That is, the computer 150 may display the GUI so that the user cannot give an instruction for concentration of the ICG outside of the foregoing numerical value range on the GUI. For example, the computer 150 may display a pull-down menu in which the user can selectively give an instruction for the concentration of the ICG within the foregoing numerical value range on the GUI. The computer 150 may configure the GUI so that the concentration of the ICG outside of the foregoing numerical value range in the pull-down menu is displayed in a gray-out manner and the gray-out concentration cannot be selected.

The computer 150 may notify of an alert when the concentration of the ICG outside of the foregoing numerical value range is instructed from the user on the GUI. As a notification method, all methods such as alert display on the display unit 160, a sound, and lamp lighting can be adopted.

The computer 150 may display the foregoing numerical value range of the concentration of the ICG introduced into the subject on the display unit 160 when the ICG is selected as the type of contrast agent on the GUI.

The concentration of the contrast agent introduced into the subject is not limited to the numerical value range described here and concentration suitable for a purpose can be adopted. Here, the example in which the type of contrast agent is the ICG has been described, but the foregoing configuration can be applied similarly to other contrast agents.

By configurating the GUI in this way, it is possible to support the user introducing the concentration of an appropriate contrast agent into the subject in accordance with the type of contrast agent scheduled to be introduced into the subject.

Next, a change in an image value corresponding to a contrast agent in a spectral image when a combination of wavelengths is changed will be described. FIGS. 9A to 9D are diagrams illustrating simulation results of image values (oxygen saturation values) corresponding to the contrast agent in the spectral image in each combination of two wavelengths. In FIGS. 9A to 9D, the vertical and horizontal axes represent first and second wavelengths, respectively. In FIG. 9, isolines of image values corresponding to the contrast agent in the spectral image are shown. FIGS. 9A to 9D show image values corresponding to the contrast agent in the spectral images when the concentration of the ICG is 5.04 µg/mL, 50.4 µg/mL, 0.5 mg/mL, and 1.0 mg/mL. As illustrated in FIGS. 9A to 9D, the image values corresponding to the contrast agent in the spectral images are 60% to 100% in accordance with combination of the selected wavelengths. As described above, when the combination of the wavelengths is selected, it is difficult to identify the blood vessel region and the contrast agent region in the spectral image. Therefore, in the combination of the wavelengths illustrated in FIGS. 9A to 9D, it is preferable to select the combination of the wavelengths in which the image value corresponding to the contrast agent in the spectral image is less than 60% or greater than 100%. In the combination of the wavelengths illustrated in FIGS. 9A to 9D, it is preferable to select the combination of the wavelengths in which the image value corresponding to the contrast agent in the spectral image is a negative value.

Figure 10:
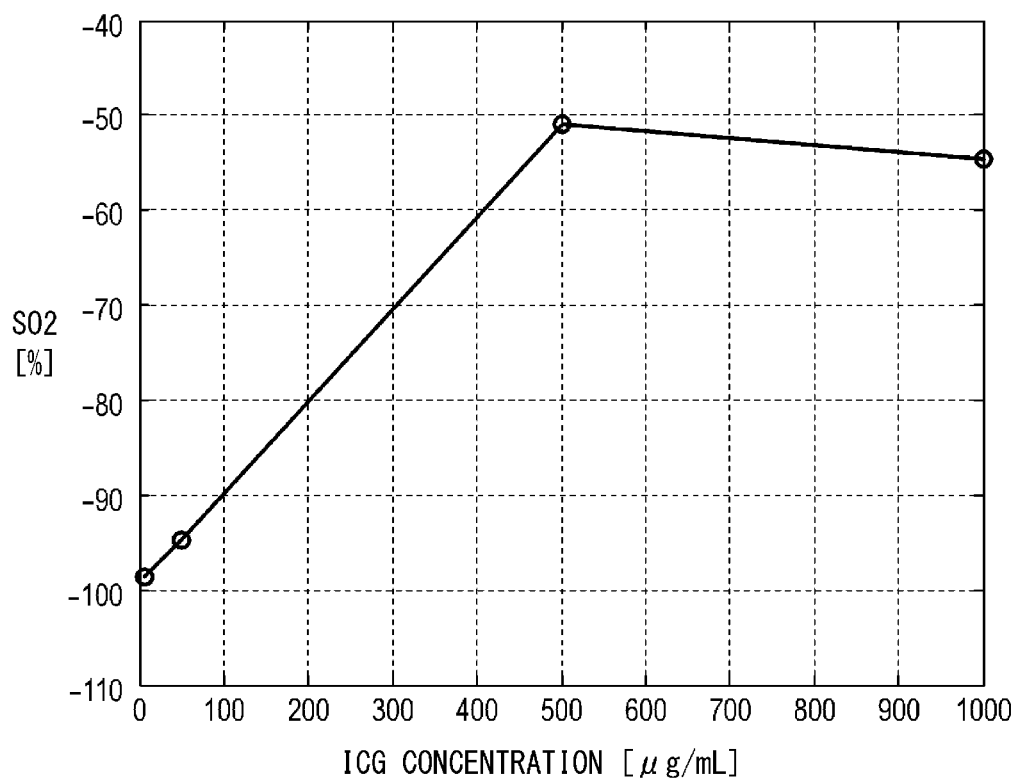
FIG. 10 is a polygonal line graph illustrating a calculation value of Expression (1) corresponding to the contrast agent when concentration of ICG is changed.

For example, a case in which 797 nm is selected as the first wavelength and 835 nm is selected as the second wavelength will be considered here. FIG. 10 is a graph illustrating a relation between the concentration of the ICG and the image value (the value of Expression (1)) corresponding to the contrast agent in the spectral image when 797 nm is selected as the first wavelength and 835 nm is selected as the second wavelength. In FIG. 10, when 797 nm is selected as the first wavelength and 835 nm is selected as the second wavelength, the image value corresponding to the contrast agent in the spectral image is a negative value at any concentration in the range of 5.04 µg/mL to 1.0 mg/mL. Therefore, since an oxygen saturation value of a blood vessel cannot be a negative value in principle in the spectral image generated in the combination of the wavelengths, the blood vessel region and the contrast agent region can be clearly identified.

Figure 11:
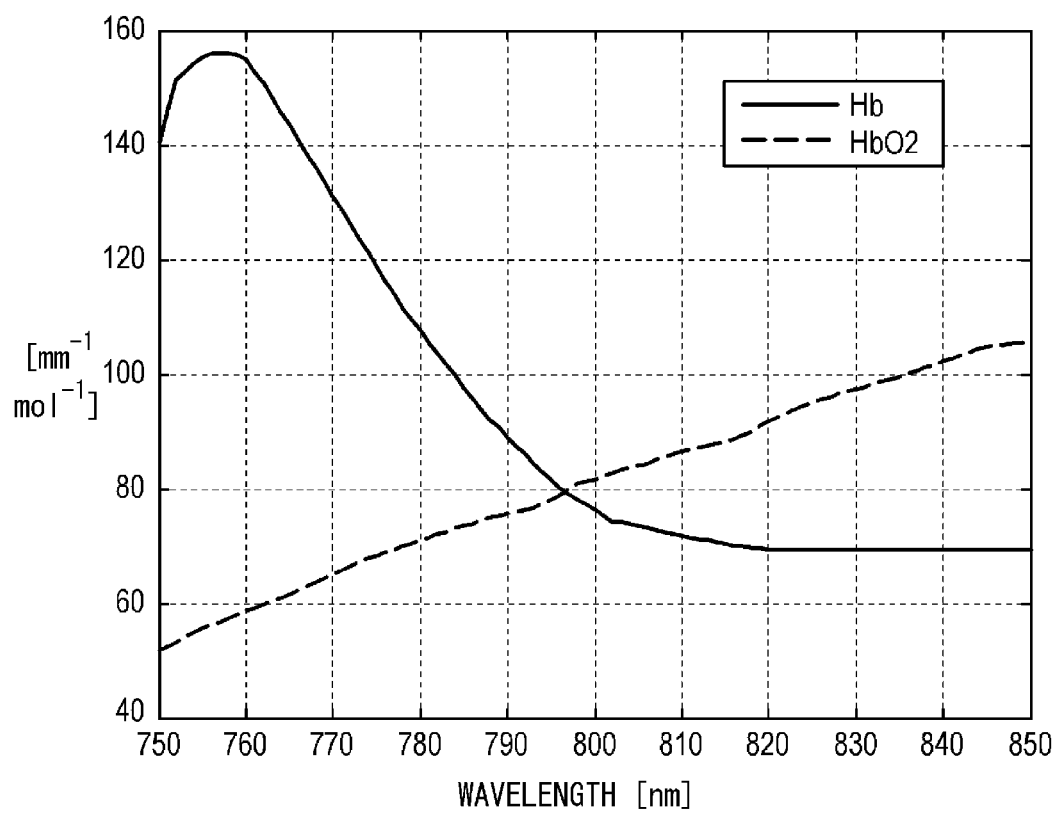
FIG. 11 is a graph illustrating a molar absorption coefficient spectrum of oxyhemoglobin and deoxyhemoglobin.

The wavelengths determined based on the information regarding the contrast agent has been described so far, but an absorption coefficient of hemoglobin may be considered in determination of the wavelengths. FIG. 11 is a diagram illustrating spectra of a molar absorption coefficient (indicated by a dotted line) of oxyhemoglobin and a molar absorption coefficient (indicated by a solid line) of deoxyhemoglobin. In a wavelength range illustrated in FIG. 11, a magnitude relation between the molar absorption coefficient of oxyhemoglobin and the molar absorption coefficient of deoxyhemoglobin is reversed at the boundary of 797 nm. That is, it is easy to ascertain a vein at a wavelength shorter than 797 nm and it is easy to ascertain an artery at a wavelength longer than 797 nm. Incidentally, treatment of lymphedema is performed in accordance with the lymphaticovenular anastomosis (LVA) for producing a bypass between a lymphatic vessel and a vein. To carry out examination before surgery, both a vein and a lymphatic vessel in which a contrast agent is accumulated are considered to be imaged by photoacoustic imaging. In this case, by causing at least one of a plurality of wavelengths to be less than 797 nm, it is possible to image the vein more clearly. In imaging of a vein, it is advantageous to cause at least one of the plurality of wavelengths in the molar absorption coefficient of deoxyhemoglobin to be greater than in the molar absorption coefficient of oxyhemoglobin. When the spectral images are generated from the photoacoustic images corresponding to two wavelengths, at both the two wavelengths in imaging of a vein, it is advantageous to cause the wavelength in the molar absorption coefficient of deoxyhemoglobin to be greater than in the molar absorption coefficient of oxyhemoglobin. By selecting such wavelengths, it is possible to image the vein and the lymphatic vessel into which the contrast agent is introduced with high accuracy in examination before surgery of the lymphaticovenular anastomosis.

Incidentally, when all the plurality of wavelengths are wavelengths at which the absorption coefficient of the contrast agent is greater than that of blood, oxygen saturation accuracy of the blood may deteriorate due to an artifact derived from the contrast agent. Accordingly, to reduce the artifact derived from the contrast agent, at least one of the plurality of wavelengths may be a wavelength at which the absorption coefficient of blood is less than the absorption coefficient of the contrast agent.

Here, the case in which the spectral images are generated by Expression (1) has been described, but the same can also apply even when the spectral image in which the image value corresponding to the contrast agent in the spectral image is changed in accordance with a condition of the contrast agent or the wavelength of radiated light is generated.

(S300: Step of Radiating Light)

The light radiation unit 110 sets the wavelength determined based on the information acquired in S100 in the light source 111. The light source 111 emits light with the determined wavelength. The light emitted from the light source 111 is radiated as pulsed light to the subject 100 via the optical system 112. The pulsed light is absorbed inside the subject 100 and a photoacoustic wave is generated due to a photoacoustic effect. At this time, the pulsed light is also absorbed by the introduced contrast agent and a photoacoustic wave is generated. The light radiation unit 110 may transmit a synchronization signal to the signal collection unit 140 along with the transmission of the pulsed light. The light radiation unit 110 similarly radiates the light with each of the plurality of wavelengths.

The user may use the input unit 170 to designate a radiation condition (a repetition frequency, a wavelength, or the like of the radiated light) of the light radiation unit 110 or a control parameter such as a position or the like of the probe 180. The computer 150 may set the control parameter determined based on the instruction from the user. The computer 150 may move the probe 180 to a designated position by controlling the driving unit 130 based on the designated control parameter. When imaging is designated at a plurality of positions, the driving unit 130 first moves the probe 180 to an initial designated position. When an instruction to start measurement is given, the driving unit 130 may move the probe 180 to a position programmed in advance.

(S400: Step of Receiving Photoacoustic Wave)

When the synchronization signal transmitted from the light radiation unit 110 is received, the signal collection unit 140 starts an operation of receiving the signal. That is, the signal collection unit 140 amplifies an analog electric signal originating from the photoacoustic wave and output from the reception unit 120 and performs AD conversion to generate an amplified digital electric signal, and outputs the digital electric signal to the computer 150. The computer 150 stores the signal transmitted from the signal collection unit 140. When imaging is designated at a plurality of scanning positions, the steps S300 and S400 are repeatedly performed at the designated scanning positions to repeat the radiation of the pulsed light and generation of received signal data which is a digital signal originating from an acoustic wave. The computer 150 may acquire and store positional information of the reception unit 120 at the time of emission of light using emission of the light as a trigger based on an output from a position sensor of the driving unit 130.

In the embodiment, the example in which each of the light with the plurality of wavelengths is radiated in a time-division manner has been described, but a method of radiating light is not limited thereto as long as signal data corresponding to each of the plurality of wavelengths can be acquired. For example, when encoding is performed by radiating light, there may be a timing at which the light with the plurality of wavelengths is substantially simultaneously radiated.

(S500: Step of Generating Three-Dimensional Photoacoustic Image)

The computer 150 serving as a three-dimensional photoacoustic image acquirer generates a photoacoustic image based on the stored signal data. The computer 150 outputs the generated photoacoustic image to the storage device 1200 to store the photoacoustic image.

A model base method (a repeated calculation method) or an analytic reconfiguration method such as a reverse projection method in a time domain or a reverse projection method in a Fourier domain can be adopted as a reconfiguration algorithm for transforming signal data into a two-dimensional or three-dimensional space distribution. For example, the reverse projection method in the time domain is Universal back-projection (UBP), Filtered back-projection (FBP), Delay-and-Sum, or the like.

The computer 150 generates an initial sound pressure distribution information (sound pressures generated at a plurality of positions) as a photoacoustic image by performing a reconfiguration process on the signal data. The computer 150 may acquire absorption coefficient distribution information as a photoacoustic image by calculating an optical fluence distribution of the light radiated to the subject 100 inside the subject 100 and dividing the initial sound pressure distribution by the optical fluence distribution. A known scheme can be applied as a scheme for calculating the optical fluence distribution. The computer 150 can generate the photoacoustic image corresponding to the light with the plurality of wavelengths. Specifically, the computer 150 can generate the first photoacoustic image corresponding to the first wavelength by performing the reconfiguration process on the signal data obtained by radiating light with the first wavelength. In addition, the computer 150 can generate the second photoacoustic image corresponding to the second wavelength by performing the reconfiguration process on the signal data obtained by radiating light with the second wavelength. In this way, the computer 150 can generate the plurality of photoacoustic images corresponding to the light with the plurality of wavelengths.

In the embodiment, one three-dimensional photoacoustic image (volume data) is generated by reconfiguring an image using the photoacoustic signal obtained when light is radiated to the subject once. Further, time-series three-dimensional image data (time-series volume data) is acquired by radiating the light a plurality of times and reconfiguring the images whenever the light is radiated. The three-dimensional image data obtained by reconfiguring the images whenever the light is radiated the plurality of times is generally termed three-dimensional image data corresponding to the radiation of the light performed the plurality of times. Since the light is radiated the plurality of times in a time-series, the three-dimensional image data corresponding to the radiation of the light performed the plurality of times configures the time-series three-dimensional image data.

In the embodiment, the computer 150 acquires the absorption coefficient distribution information corresponding to each of the pieces of light with the plurality of wavelengths as the photoacoustic images. The absorption coefficient distribution information corresponding to the first wavelength is referred to as the first photoacoustic image and the absorption coefficient distribution information corresponding to the second wavelength is referred to as the second photoacoustic image.

In the embodiment, the example of the system that includes the photoacoustic device 1100 generating the photoacoustic image has been described, but the present invention can also be applied to a system that does not include the photoacoustic device 1100. The present invention can be applied to any system as long as the image processing apparatus 1300 serving as a three-dimensional photoacoustic image acquirer can acquire a photoacoustic image. For example, the present invention can be applied to even a system that includes the storage device 1200 and the image processing apparatus 1300 without including the photoacoustic device 1100. In this case, the image processing apparatus 1300 serving as the three-dimensional photoacoustic image acquirer can acquire the photoacoustic image by reading a photoacoustic image designated among a photoacoustic image group stored in advance in the storage device 1200.

(S600: Step of Generating Three-Dimensional Spectral Image)

The computer 150 serving as the three-dimensional spectral image acquirer generates a spectral image based on a plurality of photoacoustic images corresponding to the plurality of wavelengths. The computer 150 outputs the spectral image to the storage device 1200 to store the spectral image in the storage device 1200. As described above, the computer 150 may generate a spectral image indicating information corresponding to concentration of a substance contained in a subject, such as glucose concentration, collagen concentration, melanin concentration, or a volume fraction of lipid or water. The computer 150 may generate a spectral image indicating a ratio of the first photoacoustic image corresponding to the first wavelength to the second photoacoustic image corresponding to the second wavelength. In the embodiment, an example of the computer 150 generating a spectral image that has an image value by Expression (1) using the first photoacoustic image and the second photoacoustic image will be described. The computer 150 in this step may serve as the three-dimensional spectral image acquirer. In both S500 and S600, it may be considered that the computer 150 serves as the three-dimensional photoacoustic image acquirer.

The image processing apparatus 1300 serving as the three-dimensional spectral image acquirer may acquire the spectral image by reading the spectral image designated from the spectral image group stored in advance in the storage device 1200. The image processing apparatus 1300 serving as the three-dimensional spectral image acquirer may acquire the photoacoustic image by reading at least one of the plurality of photoacoustic images used to generate the read spectral image from the photoacoustic image group stored in advance in the storage device 1200.

The time-series three-dimensional image data corresponding to the radiation of the light performed the plurality of times is generated by radiating the light the plurality of times and receiving the acoustic wave and reconfiguring the images continuously. The photoacoustic image data or the spectral image data can be used as the three-dimensional image data. Here, the photoacoustic image data indicates the image data indicating a distribution of the absorption coefficients or the like, and the spectral image data indicates the image data representing concentration or the like generated based on the photoacoustic image data corresponding to each wavelength when the light with the plurality of wavelengths is radiated to the subject.

(S700: Step of Acquiring Information Regarding Lymphatic Vessel and Blood Vessel from Three-Dimensional Image)

The image processing apparatus 1300 reads the photoacoustic image or the spectral image from the storage device 1200 and acquires the information regarding the lymphatic vessel and the blood vessel based on the photoacoustic image or the spectral image. As the acquired information, there is information indicating the positions of the lymphatic vessel and the blood vessel in the volume data. As described above, the process of this step can be performed based on the photoacoustic image originating from at least one of the wavelengths and the spectral images generated from the photoacoustic images originating from the plurality of wavelengths can also be used. In this step, the image processing apparatus 1300 functions as a three-dimensional blood vessel image acquirer and a three-dimensional lymphatic image acquirer and is in charge of information processing.

Figure 6A:
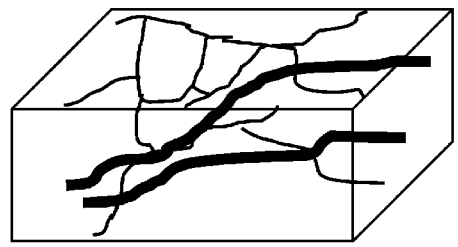
FIGS. 6A to 6C are schematic diagrams illustrating acquisition of a three-dimensional lymphatic image and a three-dimensional blood vessel image.

A method in which the three-dimensional lymphatic image acquirer performs image processing on a three-dimensional photoacoustic image originating from a single wavelength to acquire a three-dimensional lymphatic image will be described. The image processing apparatus 1300 reads the three-dimensional photoacoustic image stored in the storage device 1200. Any time range in which a target is read can be used. However, a flow of lymph is generally intermittent and a period of the flow of lymph is from tens of seconds to several minutes. Therefore, it is preferable to read a three-dimensional photoacoustic image corresponding to a photoacoustic wave acquired in a relatively long-time range. The time range may be set to, for example, 40 seconds to 2 minutes. FIG. 6A is a schematic diagram illustrating one three-dimensional photoacoustic image. Actual volume data includes an image value or the like originating from substances other than a blood vessel and a lymphatic vessel. In the drawing, however, only blood vessels and lymphatic vessels are simply displayed in volume data.

Figure 6B:
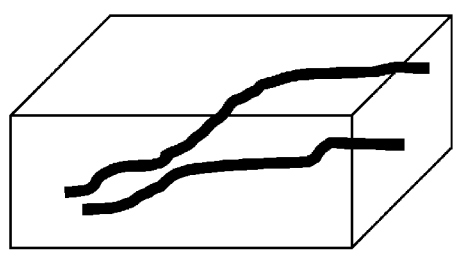

Subsequently, the image processing apparatus 1300 extracts a region in which there are lymphatic vessels from each of the read time-series three-dimensional photoacoustic images. As an example of an extraction method, there is a method in which, in view of lymph of which circulation is intermittent or periodic due to contraction of lymphatic vessels, the image processing apparatus 1300 detects a change in a luminance value in the time-series three-dimensional photoacoustic images and determines a portion in which the change in the luminance value is large as a lymphatic region. A determination criterion for a time range or a lymphatic region is exemplary and is appropriately determined in accordance with a situation of a lymphatic vessel in a subject or a condition regarding a contrast agent or radiation of light. For example, when a predetermined time range is set to 1 minute and a region that has a value of at least half of a luminance value of a general blood vessel is observed for 5 seconds of 1 minute, the region may be determined to be a lymphatic region. FIG. 6B is a schematic diagram illustrating a three-dimensional lymphatic image acquired from one three-dimensional photoacoustic image.

When a lymphatic region is extracted performing image processing on the three-dimensional spectral image instead of the three-dimensional photoacoustic image originating from the single wavelength, the image processing apparatus 1300 may extract the lymphatic region by distinguishing the region corresponding to blood from the region corresponding to the contrast agent based on the value of the oxygen saturation (the calculated value of Expression (1)). As described above, by selecting and using appropriate two wavelengths, it is possible to cause the calculated value of Expression (1) to be within an exclusive range in the region corresponding to the contrast agent and the region corresponding to blood.

Figure 6C:
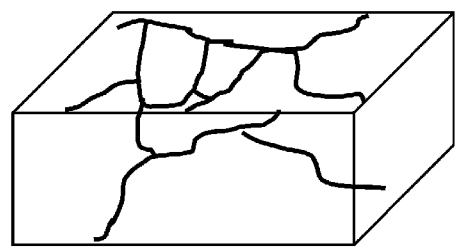

Subsequently, the image processing apparatus 1300 extracts the region in which there is a blood vessel from each of the read time-series three-dimensional photoacoustic images. For example, when a vein is selected as a target blood vessel, the region may be extracted based on the three-dimensional photoacoustic image originating from the photoacoustic wave generated by radiating the pulsed light in a region in which an absorption coefficient of deoxyhemoglobins is relatively high. FIG. 6C is a schematic diagram illustrating a three-dimensional blood vessel image acquired from one three-dimensional photoacoustic image.

When a blood vessel region is extracted by performing image processing on the three-dimensional spectral image instead of the three-dimensional photoacoustic image, the image processing apparatus 1300 may extract a blood vessel region by distinguishing the region corresponding to blood from the region corresponding to the contrast agent based on the value of the oxygen saturation. A vein may be distinguished from an artery based on the value of the oxygen saturation.

Through the process of this step, the time-series three-dimensional blood vessel image data and the time-series three-dimensional lymphatic image data, which are separated from the time-series three-dimensional photoacoustic image data, are acquired and stored in the storage device. Any method of storing the data can be used. For example, each of the three-dimensional blood vessel image data and the three-dimensional lymphatic image data may be stored as different time-series three-dimensional image data. When the single time-series three-dimensional image data is stored, the time-series three-dimensional image data may be stored at respective coordinates in the volume data in association with a flag representing that the coordinates indicate the blood vessel region, the lymphatic region, or others. The time-series three-dimensional image data may be stored in association with information regarding the wavelength of the light radiated to the subject. Any storage method does not matter as long as a two-dimensional image in which depth information is reflected in the subsequent processes of the flow can be generated.

(S800: Step of Generating Information Regarding Two-Dimensional Lymphatic Vessel and Blood Vessel and Depth Information from Information Regarding Three-Dimensional Lymphatic Vessel and Blood Vessel)

The image processing apparatus 1300 acquires information regarding a two-dimensional lymphatic region and information regarding a two-dimensional blood vessel region from the information regarding the three-dimensional lymphatic region and the information regarding the three-dimensional blood vessel region acquired in S700. In this step, the image processing apparatus 1300 functions as a two-dimensional blood vessel image acquirer and a two-dimensional lymphatic image acquirer and is in charge of information processing. Specifically, the image processing apparatus 1300 serving as the two-dimensional blood vessel image acquirer acquires two-dimensional blood vessel image data and blood vessel depth information associated with the two-dimensional blood vessel image data based on three-dimensional blood vessel image data originating from certain volume data. The image processing apparatus 1300 serving as the two-dimensional lymphatic image acquirer acquires two-dimensional lymphatic image data and lymphatic depth information associated with the two-dimensional lymphatic image data based on three-dimensional lymphatic image data originating from certain volume data. The depth information is three-dimensional positional information of a specific region in the volume data. The blood vessel depth information indicates three-dimensional positional information of a blood vessel region and the lymphatic depth information indicates three-dimensional positional information of a lymphatic region.

The image processing apparatus 1300 acquires maximum intensity projection (MIP) image data by projecting a maximum value to three-dimensional volume data in any viewpoint direction. Any projection direction of the maximum value can be used. For example, the projection direction may be a direction oriented inward a subject from the surface of a subject. In this case, the depth direction is a direction in which a depth increases toward the inside of the subject when the surface of the subject is set as a starting point. The projection direction may be a direction in accordance to coordinate axes determined depending on a configuration of the photoacoustic device. For example, when the photoacoustic device generates volume data in which three axis directions are set as a reference, the depth direction may be any of XYZ directions. When a position at which light is incident on the subject is set as a starting point as the depth direction in photoacoustic imaging, a normal direction to the surface of the subject may be adopted.

Figure 7A:
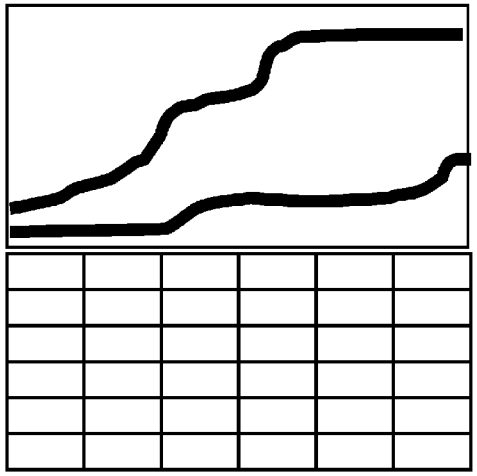
FIGS. 7A and 7B are schematic diagrams illustrating acquisition of depth information, and a two-dimensional lymphatic image and a two-dimensional blood vessel image.
Figure 7B:
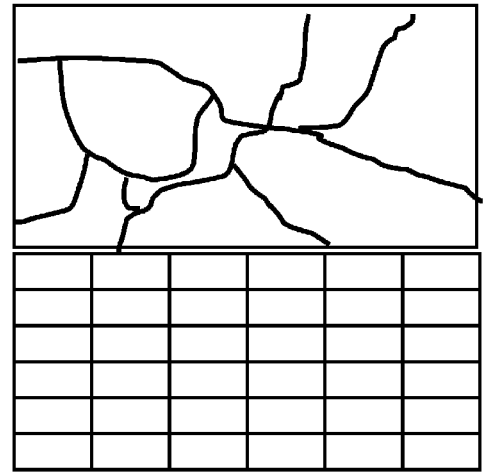

A schematic diagram of FIG. 7A illustrates a two-dimensional lymphatic image calculated by projecting a three-dimensional blood vessel image at a maximum value in the Y direction and lymphatic depth information associated with the two-dimensional lymphatic image. The lymphatic depth information includes information regarding a depth at each position at which there is a lymphatic region in an MIP image. The lymphatic depth information includes information regarding a depth at each position at which there is a lymphatic region in an MIP image. A schematic diagram of FIG. 7B is a schematic diagram illustrating a two-dimensional blood vessel image calculated by projecting a three-dimensional blood vessel image at a maximum value in the Y direction and a blood vessel depth information associated with the two-dimensional blood vessel image. In FIG. 7A, the lymphatic depth information indicates a matrix in which coordinates on the XZ plane of the two-dimensional lymphatic image are associated with coordinate information indicating a depth position in the Y direction at the coordinates. Instead of the coordinate information indicating the depth position in the Y direction, luminance, hue, brightness, and saturation associated with the coordinate information may be used. The same as FIG. 7A applies to FIG. 7B. A method applied when the two-dimensional image data is calculated from the three-dimensional image data is not limited to the maximum value projection method. Any method can be used as long as the positional information regarding presence of a lymphatic region or a blood vessel region on a two-dimensional plane and depth information regarding the lymphatic region or the blood vessel region in a viewpoint direction can be acquired. As a rendering scheme other than MIP, for example, any method such as volume rendering or surface rendering can be adopted. In any method, any setting condition such as a display region or a visual line direction when a three-dimensional image is rendered two-dimensionally can be designated in accordance with an observation target or a device configuration.

(S900: Step of Storing Two-Dimensional Image and Depth Information in Association)

The image processing apparatus 1300 serving as a storage controller stores the blood vessel depth information and the two-dimensional blood vessel image data calculated in S800 in association in the storage device 1200. The two-dimensional lymphatic image data and the lymphatic depth information are stored in association in the storage device 1200. Any storage method can be used. For example, an array in which a depth and a flag indicating whether each pixel of the two-dimensional blood vessel image data is a blood vessel are associated with each other may be used. The same applies to the two-dimensional lymphatic image data.

When the two-dimensional image data is stored in this way, an amount of data can be compressed more than the amount of three-dimensional image data. Therefore, it is possible to reduce a memory capacity of the storage device 1200. In particular, when the amount of data increasing in the case of generation in time-series volume data is reduced, a storage method in this step is effective.

(S1000: Step of Displaying Two-Dimensional Image in which Depth Information is Reflected)

The image processing apparatus 1300 serving as a display controller causes the display device 1400 to display the two-dimensional lymphatic image data in a format indicated by the lymphatic depth information. The image processing apparatus 1300 serving as the display controller causes the display device 1400 to display the two-dimensional blood vessel image data in a format indicated by the blood vessel depth information. Further, the image processing apparatus 1300 serving as the display controller may display the two-dimensional lymphatic image indicated by the lymphatic depth information and the two-dimensional blood vessel image indicated by the blood vessel depth information in a format in which a user can easily understand a correspondence relation between lymph and blood vessels. For example, the blood vessel image and the lymphatic image can be displayed in parallel or in an overlapping manner. In particular, it is preferable that the user can easily understand how deep in the lymph and the blood vessels are located.

FIG. 8A illustrates a two-dimensional lymphatic image on which brightness processing is performed based on the lymphatic depth information. FIG. 8B illustrates a two-dimensional blood vessel image on which brightness processing is performed based on the blood vessel depth information. Here, a depth is indicated in three stages, but the number of grayscales is not limited thereto. An image processing method when the image processing apparatus 1300 indicates depth information in a two-dimensional image is not limited to the brightness display. For example, at least one of brightness, saturation, and hue of a blood vessel image and a lymphatic image may be subjected to image processing to correct the depth information in a manner in which it is easy for the user to understand the depth information. In other words, a process of allocating at least one of brightness, saturation, and hue to the depth information associated with each of a blood vessel image and a lymphatic image may be performed. For example, the image processing apparatus 1300 may change tone in an image in accordance with the depth.

Here, the user wants to know a positional relation in the depth direction of a lymphatic vessel and a blood vessel in some cases. For example, to select an appropriate lymphatic vessel and blood vessel when the above-described lymphatic venule anastomosis is performed, the user searches for a pair of adjacent deep lymphatic vessel and blood vessel in some cases. Accordingly, the image processing apparatus 1300 causes the display device to display a two-dimensional lymphatic image with lymphatic depth information as in FIG. 8A and a two-dimensional blood vessel image with blood vessel depth information as in FIG. 8B in a format in which the user can easily compare the images. For example, both the images may be displayed in parallel. Both the images may be switchable with a button, a physical switch, or the like on a GUI. Both the images may be displayed in an overlapping manner as in FIG. 8C. When the user sees the overlapped and displayed images of FIG. 8C, the user can check the pair of adjacent deep lymphatic vessel and blood vessel (for example, location A or B). The image processing apparatus 1300 may detect the pair of lymphatic vessel and blood vessel located adjacently through information processing such as image analysis and present the images to the user using a marker, an arrow, or the like. With the button or the physical switch on the GUI, single display or parallel display of FIGS. 8A and 8B and display of FIG. 8C may be switched or the display may be switched by further displaying FIG. 8C in addition to single display or parallel display of FIGS. 8A and 8B.

In this way, according to the embodiment, information which the user needs can be displayed on the display device even when two-dimensional image data with the amount of data less than that of three-dimensional image data is used.

Further, according to the embodiment, the two-dimensional image data and the depth information are stored in association in S900. The image processing apparatus 1300 may generate volume data using the data and display a simple three-dimensional image on the display device. Specifically, the image processing apparatus 1300 allocates image values in two-dimensional image data in a three-dimensional space using depth information associated with the two-dimensional image data. Thus, three-dimensional images can be presented to the user even when the two-dimensional image data with a relatively small amount of data is used.

In the foregoing flow, the method of extracting the blood vessel region and the lymphatic region from the three-dimensional image data, forming the two-dimensional images of the blood vessel region and the lymphatic region, and storing and displaying the two-dimensional images has been described. However, a specific substance or a contrast agent extracted from the three-dimensional image data are not limited to the two images. As long as images can be drawn through the photoacoustic imaging, the images can be formed as the foregoing two-dimensional images and can be stored and set as display processing targets. For example, hemoglobin, myoglobin, glucose, collagen, melanin, lipid, or water can be selected as the specific substance. Further, a subdivided substance such as oxidized hemoglobin or reduced hemoglobin in hemoglobin can be set as the specific substance. A type of contrast agent is not limited to the ICG. When a drawing target is set to a first region corresponding to a first substance and a second region corresponding to a second substance, the image processing apparatus functions as a first three-dimensional image acquirer configured to acquire first three-dimensional image data in which the first region corresponding to the first substance is extracted from the three-dimensional image data, a second three-dimensional image acquirer configured to acquire second three-dimensional image data in which the second region corresponding to the second substance is extracted from the three-dimensional image data, a first two-dimensional image acquirer configured to acquire first two-dimensional image data associated with three-dimensional positional information of the first region from the first three-dimensional image data, a second two-dimensional image acquirer configured to acquire second two-dimensional image data associated with three-dimensional positional information of the second region from the second three-dimensional image data, and a storage controller configured to store the first two-dimensional image data and the second two-dimensional image data in a storage. The storage controller may store the first two-dimensional image data and the second two-dimensional image data in association in the storage.

In the foregoing example, the example in which two regions included in the three-dimensional image data are extracted and are formed as two-dimensional image data has been described, but at least three regions may be extracted from the three-dimensional image data. That is, in addition to the first and second substances, a region related to a third substance or more substances may be extracted. For example, in the three-dimensional image data expressed as the calculated value of Expression (1), as described above, the blood vessel and the lymphatic vessel can be identified since the range of the calculated value is different between the blood vessel region and the lymphatic region. Of the blood vessel regions, a vein and an artery can be separated and extracted since the calculated value of Expression (1), that is, oxygen saturation, takes a value in a different range between the vein and artery. Accordingly, as described above, three-dimensional positional information may be acquired with regard to each of the vein, the artery, and the lymphatic vessel extracted from the three-dimensional image data and two-dimensional image data associated with the three-dimensional positional information may be acquired and stored. When the vein, the artery, and the lymphatic vessel are set as three specific substances, the spectral images originating from radiation of light with two wavelengths have been used. However, depending on types of specific substances, photoacoustic data obtained by radiating light with types of wavelengths more than two can be used for separation. That is, light with the types of wavelengths less than the number of types of specific substances extracted from the three-dimensional image data may be used, or light with types of wavelengths of at least the number of extracted specific substances may be used. Even when the third substance or more substances are extracted, the image processing apparatus functions as the third three-dimensional image acquirer and the third two-dimensional image acquirer. The image processing apparatus may also function as the storage controller that stores the third two-dimensional image in association with the first two-dimensional image data and the second two-dimensional image data in the storage.

In the display step of S1000, the image processing apparatus 1300 serving as the display controller causes the display device to display the two-dimensional blood vessel image with the blood vessel depth information and the two-dimensional lymphatic image with the lymphatic depth information. The image processing apparatus according to the embodiment may display the photoacoustic image or the spectral image in addition to the display with the depth information or apart from the display with the depth information. For example, the display device may display the spectral images so that the region corresponding to the contrast agent and other regions can be identified. An example of the display will be described.

As illustrated in FIG. 12, the image processing apparatus 1300 displays a color bar 2400 as a color scale indicating a relation between an image value and a display color of a spectral image on a GUI. The image processing apparatus 1300 may determine a numerical value range of the image value allocated to the color scale based on information regarding the contrast agent (for example, information indicating that the type of contrast agent is the ICG) and information indicating the wavelength of the radiated light. For example, the image processing apparatus 1300 may determine a numerical value range including oxygen saturation of an artery, oxygen saturation of a vein, and a negative image value corresponding to the contrast agent. The image processing apparatus 1300 may determine a numerical value range of –100% to 100% and set the color bar 2400 in which –100% to 100% are allocated to color gradation changed from blue to red. According to the display method, a region corresponding to a contrast agent with a negative value can also be identified in addition to the identification of a vein and an artery. The image processing apparatus 1300 may display an indicator 2410 indicating a numerical value range of the image value corresponding to the contrast agent based on information regarding the contrast agent and information regarding the wavelength of the radiated light. Here, in the color bar 2400, a region with a negative value which is a numerical value range of the image value corresponding to the ICG is indicated by the indicator 2410. By displaying a color scale so that a display color corresponding to the contrast agent can be identified, it is possible to easily identify the region corresponding to the contrast agent in the spectral image.

The image processing apparatus 1300 serving as a region determiner may determine the region corresponding to the contrast agent in the spectral image based on the information regarding the contrast agent and the information indicating the wavelength of the radiated light. For example, the image processing apparatus 1300 may determine a region that has a negative image value as the region corresponding to the contrast agent in the spectral image. The image processing apparatus 1300 may cause the display device 1400 to display the spectral image so that the region corresponding to the contrast agent and the other regions can be identified. The image processing apparatus 1300 can adopt identification display such as display of an indicator (for example, a frame) indicating the region corresponding to the contrast agent and flickering the region corresponding to the contrast agent so that display colors of the region corresponding to the contrast agent and the other regions are different.

The display may be switched to a display mode in which the image value corresponding to the ICG can be selectively displayed by giving an instruction for an item 2730 corresponding to the display of the ICG displayed on the GUI illustrated in FIG. 12. For example, the region of the ICG may be selectively displayed by causing the image processing apparatus 1300 to select voxels with a negative image value from the spectral image and selectively render the selected voxels when the user selects the item 2730 corresponding to the display of the ICG. Similarly, the user may select an item 2710 corresponding to display of an artery or an item 2720 corresponding to display of a vein. Based on an instruction from the user, the image processing apparatus 1300 may switch the display to a display mode in which an image value (which is, for example, at least 90% and not more than 100%) corresponding to the artery or an image value (which is, for example, at least 60% and less than 90%) corresponding to the vein is selectively displayed. The numerical value range of the image value corresponding to the artery or the image value corresponding to the vein may be changed based on an instruction from the user.

Images in which at least one of hue, brightness, and saturation is allocated to an image value of the spectral image and the remaining parameters of hue, brightness, and saturation are allocated to an image value of the photoacoustic image may be displayed as spectral images. For example, images in which hue and saturation are allocated to the image value of the spectral image and brightness is allocated to the image value of the photoacoustic image may be displayed as the spectral images. At this time, when the image value of the photoacoustic image corresponding to a contrast agent is greater or less than the image value of the photoacoustic image corresponding to a blood vessel and brightness is allocated to the image value of the photoacoustic images, it is difficult to view both the blood vessel and the contrast agent in some cases. Accordingly, in accordance with the image value of the spectral image, a conversion table may be changed from the image value of the photoacoustic image to brightness. For example, when the image value of the spectral image is included in the numerical value range of the image value corresponding to the contrast agent, brightness corresponding to the image value of the photoacoustic image may be less than brightness corresponding to the blood vessel. That is, when the contrast agent region and the blood vessel region are compared and the image values of the photoacoustic images are the same, brightness of the contrast agent region may be less than brightness of the blood vessel region. Here, the conversion table is a table that shows brightness corresponding to each of a plurality of image values. When the image value of the spectral image is included in the numerical value range of the image value corresponding to the contrast agent, brightness corresponding to the image value of the photoacoustic image may be caused to be greater than brightness corresponding to the blood vessel. That is, when the contrast agent region and the blood vessel region are compared and the image values of the photoacoustic images are the same, the brightness of the contrast agent region may be caused to be greater than in the blood vessel region. In accordance with the image value of the spectral image, the numerical value range of the image values of the photoacoustic images in which the image value of the photoacoustic image is not changed into brightness may differ.

The conversion table may be changed into an appropriate conversion table in accordance with the type or concentration of the contrast agent and the wavelength of the radiated light. Accordingly, the image processing apparatus 1300 may determine the conversion table from the image value of the photoacoustic image to brightness based on information indicating the contrast agent and information regarding the wavelength of the radiated light. When the image value of the photoacoustic image corresponding to the contrast agent is estimated to be greater than that corresponding to the blood vessel, the image processing apparatus 1300 may cause the brightness corresponding to the image value of the photoacoustic image corresponding to the contrast agent to be less than that corresponding to the blood vessel. Conversely, when the image value of the photoacoustic image corresponding to the contrast agent is estimated to be less than that corresponding to the blood vessel, the image processing apparatus 1300 may cause the brightness corresponding to the image value of the photoacoustic image corresponding to the contrast agent to be greater than that corresponding to the blood vessel.

On the GUI illustrated in FIG. 12, an absorption coefficient image (the first photoacoustic image) 2100 corresponding to a wavelength of 797 nm, an absorption coefficient image (the second photoacoustic image) 2200 corresponding to a wavelength of 835 nm, and an oxygen saturation image (a spectral image) 2300 are displayed. Whether each image is an image generated using light with a certain wavelength may be displayed on the GUI. In the embodiment, both the photoacoustic image and the spectral image are displayed, but only the spectral image may be displayed. The image processing apparatus 1300 may switch display of the photoacoustic image and display of the spectral image based on an instruction from the user.

The display unit 160 may be able to display a moving image. For example, the image processing apparatus 1300 may be configured to generate at least one of the first photoacoustic image 2100, the second photoacoustic image 2200 and the spectral image 2300 in a time-series manner, generate moving-image data based on the generated time-series images, and output the moving-image data to the display unit 160. In view of lymph of which a flow is relatively less frequently, it is also preferable to display a still image or a time-compressed moving image in order to shorten a determination time of the user. In the moving-image display, an aspect of the flow of lymph can also be displayed repeatedly. A speed of the moving image may be a predetermined speed regulated in advance or a predetermined speed designated by the user.

In the display unit 160 capable of displaying a moving image, a frame rate of the moving image is preferably variable. In order to cause the frame rate to be variable, a window used for the user to manually input the frame rate, a slide bar used for the user to change the frame rate, or the like may be added to the GUI of FIG. 12. Here, since lymph flows intermittently inside a lymphatic vessel, only a part of the acquired time-series volume data can be used to check the flow of lymph. Therefore, when real-time display is performed at the time of checking of the flow of lymph, efficiency deteriorates in some cases. Accordingly, when a frame rate of a moving image displayed on the display unit 160 is caused to be variable and the displayed moving image can be displayed in a fast forward manner, the user can check an aspect of a fluid inside the lymphatic vessel in a short time.

The display unit 160 may be able to repeatedly display a moving image within a predetermined time range. At this time, it is also preferable to add a GUI such as a window or a slide bar used for the user to designate a range in which the repeated display is performed, to FIG. 12. Thus, for example, the user easily ascertains the aspect of a fluid flowing inside the lymphatic vessel.

As described above, at least one of the image processing apparatus 1300 and the computer 150 serving as an information processing device functions as a device that includes at least one of a spectral image acquirer, a contrast agent information acquirer, a region determiner, a photoacoustic image acquirer, and a display controller. Each unit may be configured by different hardware or may be configured by single hardware. The plurality of units may be configured by single hardware.

In the embodiment, a blood vessel and a contrast agent can be identified by selecting the wavelength in which the image value corresponding to the contrast agent has a negative value. However, the image value corresponding to the contrast agent may be any value as long as the blood vessel and the contrast agent can be identified in accordance with the image value corresponding to the contrast agent. For example, even when the image value of the spectral image (an oxygen saturation image) corresponding to the contrast agent is less than 60% or greater than 100%, the image processing described in the step can be applied.

Other Embodiments

Additionally, the present invention can be achieved by performing the following processes. Namely, software (program) for achieving the functions as described in the above embodiments is provided for a system or an apparatus via a network or various storage media and the processes are processes which a computer (or a CPU or a MPU etc.) of the system or the apparatus read out and execute the program to perform.

It is to be understood that the invention is not limited to the disclosed exemplary embodiments and modifications or variations can be applied to the above embodiments without exceeding the scope of the disclosure. The following claims are attached in order to disclose the scope of the disclosure.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

According to the present invention, it is possible to provide a technology capable of further reducing an amount of data in photoacoustic imaging than in the related art.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An image processing apparatus processing three-dimensional image data generated based on a photoacoustic wave generated from inside of a subject by radiating light to the subject, the image processing apparatus comprising:
   a memory configured to store a program; and
   one or more processors which are configured to, by executing the program, function as a plurality of units comprising:
   (1) a first three-dimensional image acquisition unit configured to acquire first three-dimensional image data in which a blood vessel region corresponding to a first substance in the subject is extracted from the three-dimensional image data;
   (2) a second three-dimensional image acquisition unit configured to acquire second three-dimensional image data in which a lymphatic region corresponding to a second substance different from the first substance in the subject is extracted from the three-dimensional image data;
   (3) a first two-dimensional image acquisition unit configured to acquire, from the first three-dimensional image data, (a) first two-dimensional image data of the blood vessel region and (b) first depth position data of each part of the blood vessel region in a first depth direction, the first depth direction being a direction oriented inward with respect to the subject;
   (4) a second two-dimensional image acquisition unit configured to acquire, from the second three-dimensional image data, (a) second two-dimensional image data of the lymphatic region and (b) second depth position data of each part of the lymphatic region in a second depth direction, the second depth direction being a direction oriented inward with respect to the subject; and
   (5) a display control unit configured to combine and display (a) the first two-dimensional image data in accordance with the first depth position data and (b) the second two-dimensional image data in accordance with the second depth position data.

2. The image processing apparatus according to claim 1, wherein the plurality of units further comprises a storage control unit configured to store, in a storage unit, the first two-dimensional image data and the second two-dimensional image data.

3. The image processing apparatus according to claim 2, wherein the storage control unit is configured to store, in the storage unit, the first two-dimensional image data and the second two-dimensional image data in association with each other.

4. The image processing apparatus according to claim 1, the display control unit is configured to display, on a display device, a first two-dimensional image based on the first two-dimensional image data and a second two-dimensional image based on the second two-dimensional image data.

5. The image processing apparatus according to claim 4, wherein the display control unit is configured to perform image processing on the first two-dimensional image on the basis of the first depth position data and on the second two-dimensional image on the basis of the second depth position data.

6. The image processing apparatus according to claim 5, wherein the display control unit is configured to perform image processing of correcting at least one of brightness, saturation, and hue of (a) the first two-dimensional image on the basis of the first depth position data and (b) the second two-dimensional image on the basis of the second depth position data.

7. The image processing apparatus according to claim 4, wherein the display control unit is configured to display on the display device the first two-dimensional image and the second two-dimensional image in accordance with at least one method of (1) parallel display, (2) superimposing display, and (3) switching display.

8. The image processing apparatus according to claim 4, wherein the display control unit is configured to display on the display device (1) a three-dimensional image generated from the first two-dimensional image data in accordance with the first depth position data and (2) a three-dimensional image generated from the second two-dimensional image data in accordance with the second depth position data.

9. The image processing apparatus according to claim 4, wherein the display control unit is configured to display a plurality of the first two-dimensional images and a plurality of the second two-dimensional images generated in a time series as a moving image.

10. The image processing apparatus according to claim 9, wherein the display control unit is configured so as to be able to display the moving image in a fast-forward manner.

11. The image processing apparatus according to claim 9, wherein the display control unit is configured so as to be able to display the moving image repeatedly.

12. The image processing apparatus according to claim 1, wherein the three-dimensional image data is photoacoustic image data originating from a photoacoustic wave generated from the inside of the subject by radiating light.

13. The image processing apparatus according to claim 1, wherein the three-dimensional image data is a spectral image generated based on (1) a first photoacoustic image, which is based on a photoacoustic wave generated by radiating light having a first wavelength, and (2) a second photoacoustic image, which is based on a photoacoustic wave generated by radiating light having a second wavelength.

14. The image processing apparatus according to claim 1, wherein the three-dimensional image data is time-series three-dimensional image data including an image which is generated based on photoacoustic waves generated by radiating light to the subject a plurality of times and corresponds to the radiation of light performed a plurality of times.

15. The image processing apparatus according to claim 1, wherein the plurality of units further comprises:
   a third three-dimensional image acquisition unit configured to acquire third three-dimensional image data in which a third region corresponding to a third substance in the subject is extracted from the three-dimensional image data; and a third two-dimensional image acquisition unit configured to acquire, from the third three-dimensional image data, (a) third two-dimensional image data of the third region and (b) third depth position data of each part of the third region in a third depth direction, the third depth direction being a direction oriented inward with respect to the subject.

16. The image processing apparatus according to claim 1, wherein the first depth direction is perpendicular to a surface of the subject in the first three-dimensional image data and the second depth direction is perpendicular to a surface of the subject in the second three-dimensional image data.

17. The image processing apparatus according to claim 1, wherein the first two-dimensional image data is a first projection image generated by projecting the first three-dimensional image data at a maximum value in a depth direction of the first three-dimensional image data, and wherein the second two-dimensional image data is a second projection image generated by projecting the second three-dimensional image data at a maximum value in a depth direction of the second three-dimensional image data.

18. An image processing method, performed by a processor executing a program stored in a memory, of processing three-dimensional image data generated based on a photoacoustic wave generated from inside of a subject by radiating light to the subject, the method comprising:

a step of acquiring first three-dimensional image data in which a blood vessel region corresponding to a first substance in the subject is extracted from the three-dimensional image data;

a step of acquiring second three-dimensional image data in which a lymphatic region corresponding to a second substance different from the first substance in the subject is extracted from the three-dimensional image data;

a step of acquiring, from the first three-dimensional image data, (a) first two-dimensional image data of the blood vessel region and (b) first depth position data of each part of the blood vessel region in a first depth direction, the first depth direction being a direction oriented inward with respect to the subject;

a step of acquiring, from the second three-dimensional image data, (a) second two-dimensional image data of the lymphatic region and (b) second depth position data of each part of the lymphatic region in a second depth direction, the second depth direction being a direction oriented inward with respect to the subject; and a step of combining and displaying (a) the first two-dimensional image data in accordance with the first depth position data and (b) the second two-dimensional image data in accordance with the second depth position data.

19. A non-transitory computer-readable medium that stores a program for causing a computer to execute the image processing method according to claim 18.

* * * * *